US012262751B2

(12) United States Patent
Brunner et al.

(10) Patent No.: US 12,262,751 B2
(45) Date of Patent: Apr. 1, 2025

(54) CARB CAP FOR VAPORIZATION ASSEMBLY, PORTABLE VAPORIZATION DEVICE, AND METHODS OF USE

(71) Applicant: Puff Corporation, Los Angeles, CA (US)

(72) Inventors: Douglas Brunner, Pasadena, CA (US); Avinash Bajpai, Aguora Hills, CA (US); Siddhant Waghmare, Los Angeles, CA (US); Charlton Huang, Irvine, CA (US); Roger Sayre, Los Angeles, CA (US)

(73) Assignee: Puff Corporation, Los Angeles, CA (US)

( * ) Notice: Subject to any disclaimer, the term of this patent is extended or adjusted under 35 U.S.C. 154(b) by 0 days.

(21) Appl. No.: 18/631,454

(22) Filed: Apr. 10, 2024

(65) Prior Publication Data

US 2024/0365872 A1 Nov. 7, 2024

Related U.S. Application Data

(60) Provisional application No. 63/458,536, filed on Apr. 11, 2023.

(51) Int. Cl.
*A24F 40/485* (2020.01)
*A24F 40/42* (2020.01)
*A24F 40/46* (2020.01)
*A24F 40/60* (2020.01)
*H05B 3/04* (2006.01)

(52) U.S. Cl.
CPC ............ *A24F 40/485* (2020.01); *A24F 40/42* (2020.01); *A24F 40/46* (2020.01); *A24F 40/60* (2020.01); *H05B 3/04* (2013.01)

(58) Field of Classification Search
CPC .......... A24F 40/485; A24F 5/10; A24F 40/20; A24F 40/40; A24F 40/42; A24F 40/46; H05B 3/04
See application file for complete search history.

(56) References Cited

U.S. PATENT DOCUMENTS

| 7,782,306 B2 | 8/2010 | Guo et al. |
| 9,764,230 B2 | 9/2017 | Gassoway et al. |
| 10,021,905 B1 * | 7/2018 | Bebee .................. F04B 39/123 |

(Continued)

FOREIGN PATENT DOCUMENTS

WO 2022236082 A1 11/2022

OTHER PUBLICATIONS

Original Peak with Ball Cap, Post on Reddit, 2022.

(Continued)

*Primary Examiner* — Hae Moon Hyeon
(74) *Attorney, Agent, or Firm* — Bryan Cave Leighton Paisner LLP

(57) ABSTRACT

Aspects of the present invention relate to a carb cap for a portable electronic vaporizing device for use in the vaporization of substances. The carb cap comprises a vaporization assembly attachment, a movable gas introduction stem, and a flexible diaphragm extending between the movable gas introduction stem and the vaporization assembly attachment. Methods of using such carb cap with a portable electronic vaporizing device and a vaporization assembly that is compatible with the device are provided.

29 Claims, 15 Drawing Sheets

(56) References Cited

U.S. PATENT DOCUMENTS

| | | | |
|---|---|---|---|
| 11,140,924 B1 | 10/2021 | Bajpai et al. | |
| 11,375,752 B1 * | 7/2022 | Bajpai | A61M 15/0021 |
| 11,659,865 B2 * | 5/2023 | Bajpai | A24F 40/48 |
| | | | 131/329 |
| 2017/0055579 A1 | 3/2017 | Kuna et al. | |
| 2018/0098569 A1 * | 4/2018 | Martin | A61M 15/06 |

OTHER PUBLICATIONS

Pulsar Quartz Banger & Ball Carb Cap Set—Colors Vary—World of Bongs, 2022.
Peak Pro with Ball Cap, Instagram, 2021.
Spacewalk N64 Joystick, Post on Reddit, 2020.
Puffco Peak Ball Cap, Instagram, 2018.

* cited by examiner

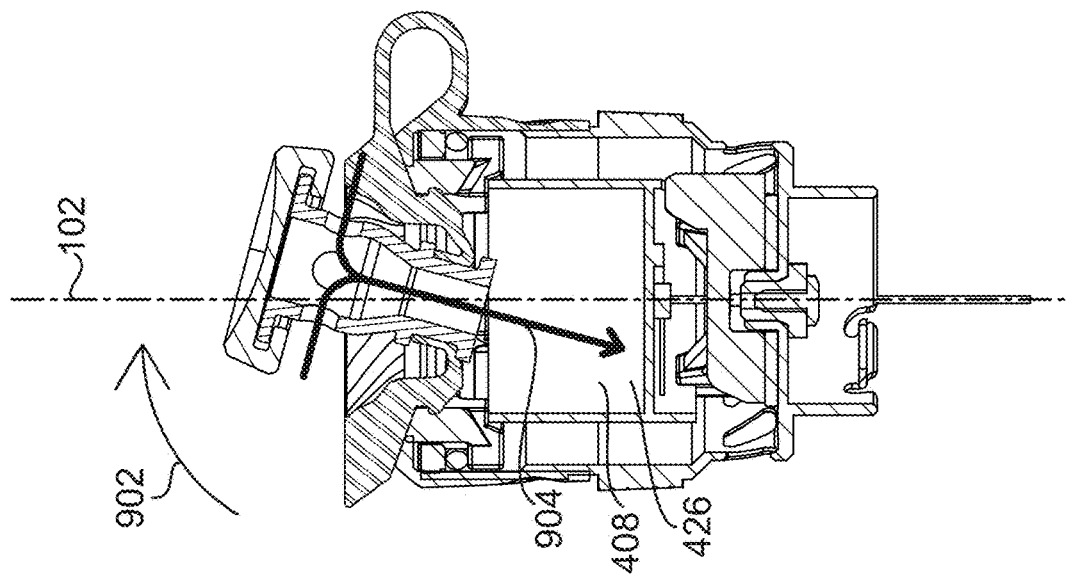
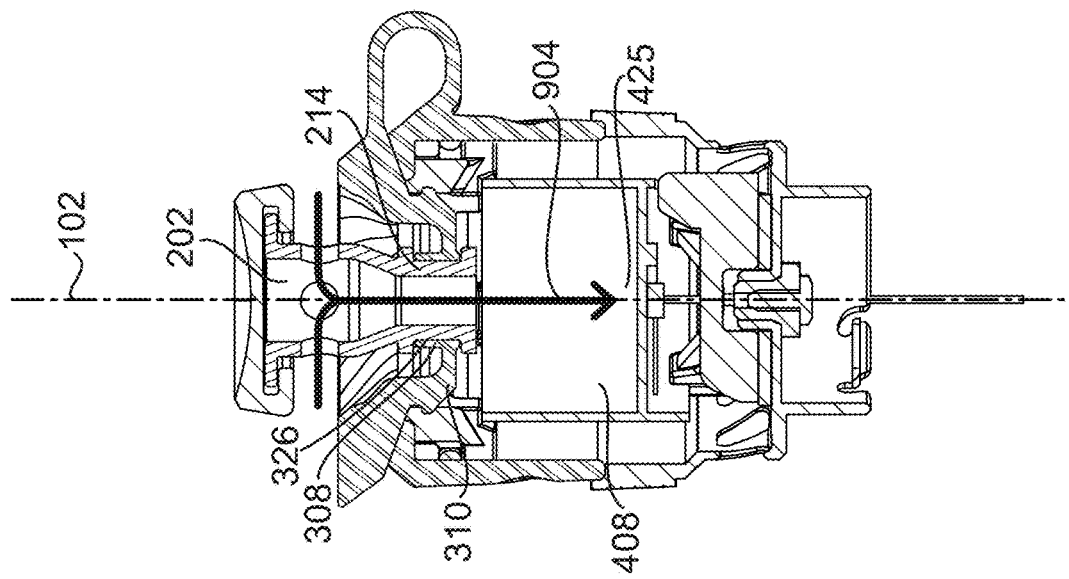
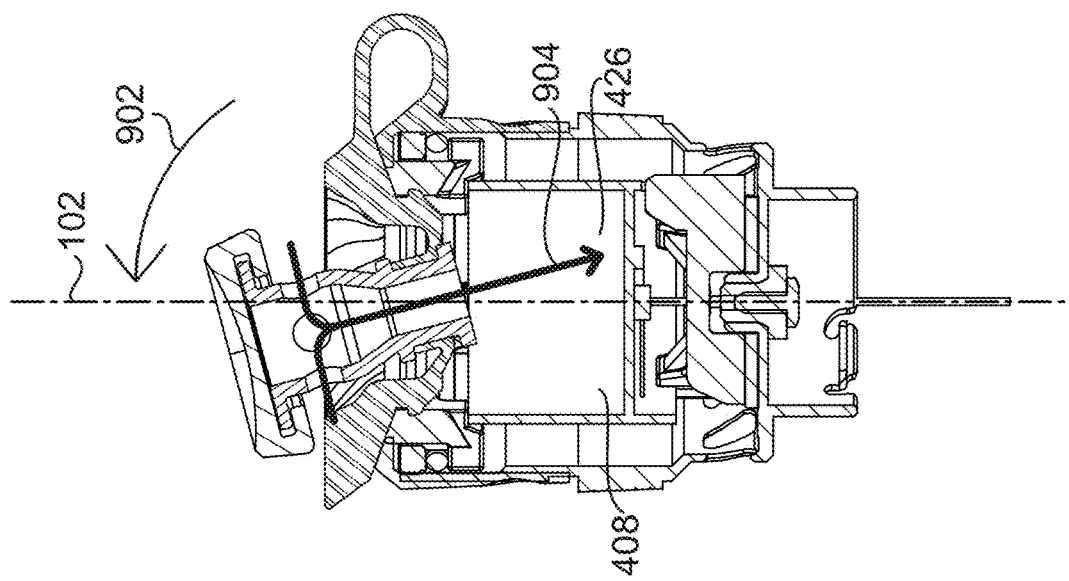

CARB CAP FOR VAPORIZATION ASSEMBLY, PORTABLE VAPORIZATION DEVICE, AND METHODS OF USE

CROSS-REFERENCE TO RELATED APPLICATIONS

The present application claims benefit to U.S. Provisional Patent Application No. 63/458,536, filed Apr. 11, 2023. The entire content of the above application is incorporated by reference as if recited in full herein.

FIELD OF THE INVENTION

Aspects of the present invention relate to embodiments of a carb cap for a vaporization assembly for use with a portable electronic vaporizing device.

BACKGROUND

Electronic vaporizers are commonplace and are generally utilized for the purpose of aroma and/or inhalation therapy. In this regard, vaporizers heat a substance, herbs for example, such as tobacco, *cannabis*, lavender, chamomile, and many other types of plant material. The vaporizer may work by heating the substance through the use of direct heat or the use of hot air. There are three common ways of heating the substance. The first is thermal conduction where the substance is set directly on a heating element such as a ceramic or metal plate. The second is thermal radiation in which light is used to heat the substance. The third is convection where hot air is passed over the substance. Yet another suitable mechanism for vaporizing a substance may be via inductive heating.

At lower levels of heat, vapors extracted from substances such as vegetable materials are mainly aroma therapeutic (inactive fragrance) and do not usually contain the active ingredients of the substance. Without the active ingredients being present, there is no physiological reaction. At higher levels of heat, active ingredients will be increasingly included in the vapor given off during heating. Usually, aromatic vapors have already been released and are not always present at the higher heat levels. With some substances, such as *cannabis*, active ingredients appear at different levels of heat.

After the substance is heated a mist or vapor containing some aspect of the substance is released and either enjoyed as an aromatic or inhaled to obtain a physiological reaction. The warm air containing the substance product can be harsh on the throat and bronchial tubes. Accordingly, some vaporizers use a cooling down process that allows water moisture to be included in the vapor produced. These vaporizers enable the user to inhale a cool moist vapor that is relatively less harsh and irritating. Vaporizers are often preferred over traditional methods of heating or smoking substances due to the reduction of harsh side effects. Some of these side effects include inhalation of tar, carbon monoxide, and other carcinogens either directly or from secondhand smoke. With many states imposing smoking bans in public areas, vaporizers have become popular substitutes.

There is a need to more effectively deliver gas into the vaporizer, to better direct the flow of gas into the vaporizer, and to improve the quality and efficiency of the vapor production for inhalation which would lead to an improved ease of use of the vaporizer generally.

SUMMARY

Aspects of the present disclosure are directed to a carb cap for a vaporization assembly. The carb cap comprises: a vaporization assembly attachment configured to be attached to a vaporization assembly, a movable gas introduction stem configured to introduce gas into the vaporization assembly, and a flexible diaphragm extending in between the movable gas introduction stem and the vaporization assembly attachment. The movable gas introduction stem comprises: one or more gas inlets located towards a first end of the movable gas introduction stem configured to receive a flow of gas, a gas outlet located towards a second end of the movable gas introduction stem configured to introduce the flow of gas into the vaporization assembly, and a gas flow conduit through the movable gas introduction stem connecting the one or more gas inlets to the gas outlet.

According to another aspect of the present disclosure, a portable electronic vaporizing device is provided that comprises a vaporization assembly and a carb cap according to embodiments of the disclosure herein. According to yet another aspect of the present disclosure, a vaporization assembly is provided that comprises a carb cap according to embodiments of the disclosure herein.

According to another aspect of the invention, a method of introducing gas flow into a vaporization assembly is provided. The method comprises: attaching a carb cap disclosed herein to a vaporization assembly of a vaporization device, and during operation of the vaporization device, moving the movable gas introduction stem to direct a flow of gas entering a vaporization assembly housing.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 9A depicts a cross-section taken along line 3 of FIG. 2A and shows an embodiment of a vaporization assembly having a carb cap according to aspects of the present disclosure in response to force being applied to a movable gas introduction stem.

FIG. 9B depicts a cross-section taken along line 3 of FIG. 2A and shows an embodiment of a vaporization assembly having a carb cap according to aspects of the present disclosure when no force is being applied to a movable gas introduction stem.

FIG. 9C depicts a cross-section taken along line 3 of FIG. 2A and shows an embodiment of a vaporization assembly having a carb cap according to aspects of the present disclosure in response to force being applied to a movable gas introduction stem.

DETAILED DESCRIPTION OF THE INVENTION

Figure 1:
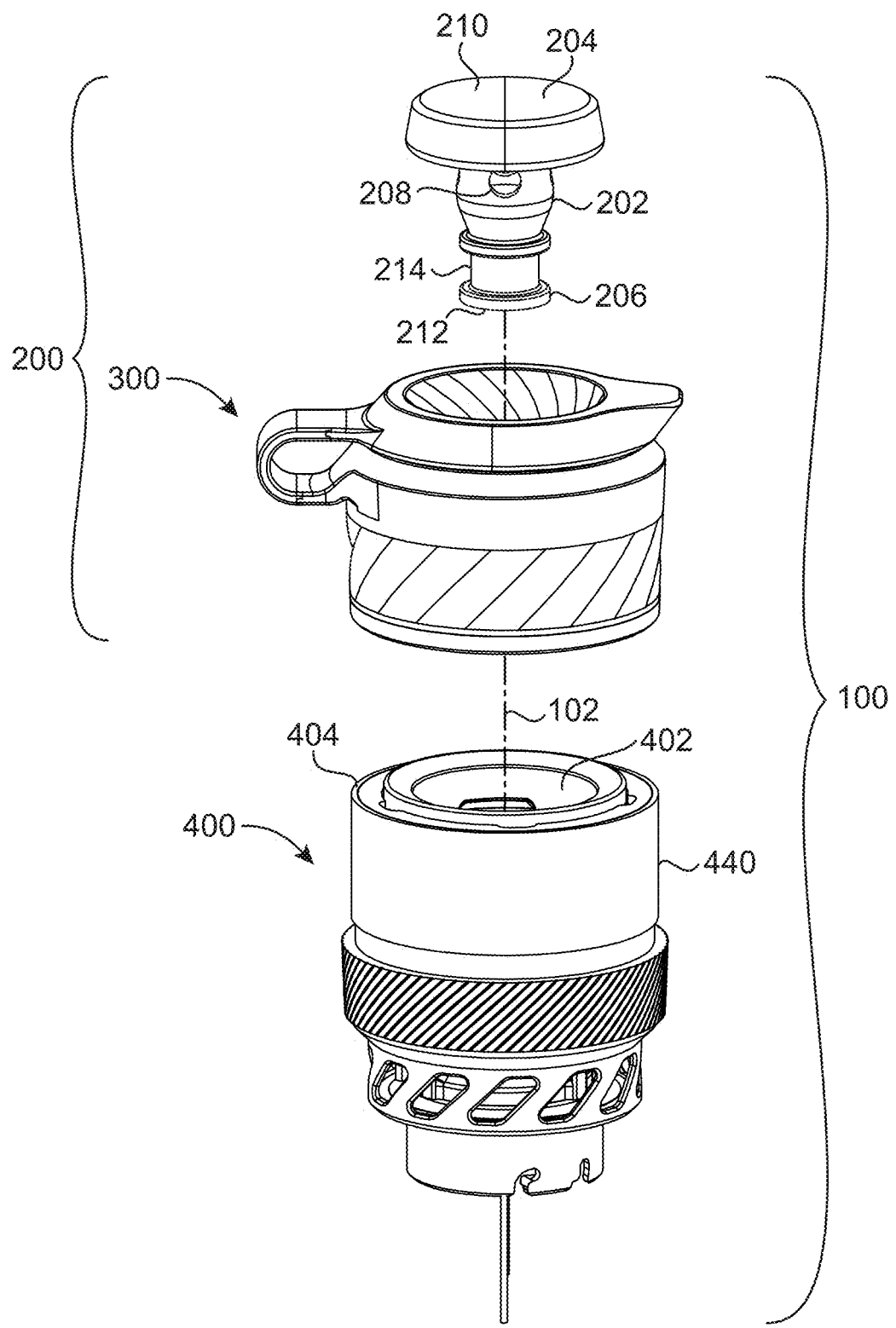
FIG. 1 is an exploded view of an embodiment of a vaporization assembly having a carb cap according to aspects of the present disclosure.

Aspects of the invention as described herein are directed to an improved carb cap for a vaporization assembly of a portable electronic vaporizing device, for the inhalation of vaporizable substances, such as aromatic substances, therapeutic substances and/or substances with physiological effects. Examples of such substances can include herbs, such as tobacco, *cannabis*, lavender, chamomile, and other types of plant material. In one embodiment, a vaporizable substance can comprise a cannabinoid, such as for example one or more of cannabidiol (a generally non-psychoactive therapeutic substance) and tetrahydrocannabinol (THC) (a psychoactive therapeutic substance). The vaporizable substance may in some embodiments be in the form of an oil and/or wax product comprising the vaporizable substance, e.g., as extracted from plant material containing the substance, and may optionally be provided in combination with carriers or other additives.

Carb caps can be used to provide a controlled flow of gas into a vaporization assembly and to a vaporizable product held therein, to provide for improved vaporization of the product during use of a portable vaporization device. According to certain embodiments, the carb cap can be provided over an opening of the vaporization assembly, to serve as a cover or lid that at least partly isolates the interior of the vaporization assembly and the vaporizable product held therein from the ambient environment. The carb cap includes a gas flow conduit that communicates with the ambient environment, such that a flow of gas from the ambient environment enters the vaporization assembly through the gas flow conduit upon inhalation by a user at a mouthpiece of the portable vaporization device, or other negative pressure exerted on the gas flow in the vaporization assembly. According to certain embodiments, gas flow parameters such as the gas flow velocity and the position, direction and/or angle of flow into the vaporization assembly, can be determined by selecting the configuration of the carb cap and/or conduit used to introduce gas into the vaporization assembly, with the velocity of gas from the ambient environment typically being increased via introduction through the conduit. For example, according to certain embodiments, the shape and configuration of the carb cap and its gas flow conduit can be selected to control the velocity and/or direction of gas flow into the vaporization assembly, to enhance the contact of the gas flow with the vaporizable product held in the vaporization assembly and enhance the vaporization of the product.

According to certain embodiments herein, a carb cap 200 is provided that allows for a directional introduction of gas into a vaporization assembly 400, to improve the vaporization of a vaporizable product held therein. As shown for example in FIG. 1 to 3, embodiments of the carb cap 200 incorporate a flexible diaphragm 306 that is engaged with a movable gas introduction stem 202 that introduces into the vaporization assembly, and which allows the movable gas introduction stem 202 to rotate and/or move with respect to a central axis 102 of the carb cap, to provide for the introduction of gas into the vaporization assembly 400 at multiple different angles and at different positions within the vaporization assembly 400, according to a user's preference. For example, according to certain embodiments, the movable gas introduction stem 202 can be rotated and/or moved to introduce the flow of gas towards the sides of a container 408 holding the vaporizable product, to target product at locations in the container 408 that may be otherwise difficult to direct gas towards without a directional flow of gas. As another example, according to certain embodiments the movable gas introduction stem 202 can be rotated and/or moved to spread vaporizable product along exposed surfaces of the container 408, thereby reducing the thickness of the product layer held on the bottom of the container 408 and improving vaporization of the product. That is, embodiments of the carb cap 200 may be capable of providing a directional flow of gas into the vaporization assembly 400, e.g., a flow of gas with a gas flow direction and/or angle into the vaporization assembly 400, that is selected by the user by manipulation of the movable gas introduction stem 202.

Furthermore, certain embodiments of the carb cap 200 may be capable of providing a directional flow of gas into the vaporization assembly 400 with reduced incidence of sticking or gumming up of the movable gas introduction stem 202 from splash-back by vaporizable product held in the container 408. For example, the carb cap 200 may be capable of providing for rotation and/or movement of the movable gas introduction stem 202 substantially without requiring translation of the movable gas introduction stem 202 against other surfaces of the carb cap 200, which surfaces might otherwise be vulnerable to becoming gummed up or stuck together in the event of product back-splash. According to embodiments herein, since the flexible diaphragm 306 is capable of imparting movement to the moveable gas introduction stem 202, substantially without requiring surfaces of the moveable gas introduction stem 202 to slide or rotate with respect to surfaces of the flexible diaphragm 306 or other carb cap surfaces to achieve movement, the vulnerability of the carb cap 200 to gumming up or inhibition of movement is reduced. Embodiments of the carb cap 200 may thus provide that product splash-back onto the inside of the carb cap 200 substantially does not substantially inhibit rotation and/or movement of the movable gas introduction stem 202, because accumulation of such splash-back on the interior of the carb cap 200 does not greatly affect the ability of the moveable gas introduction stem 202 to rotate and/or move.

Figure 2A:
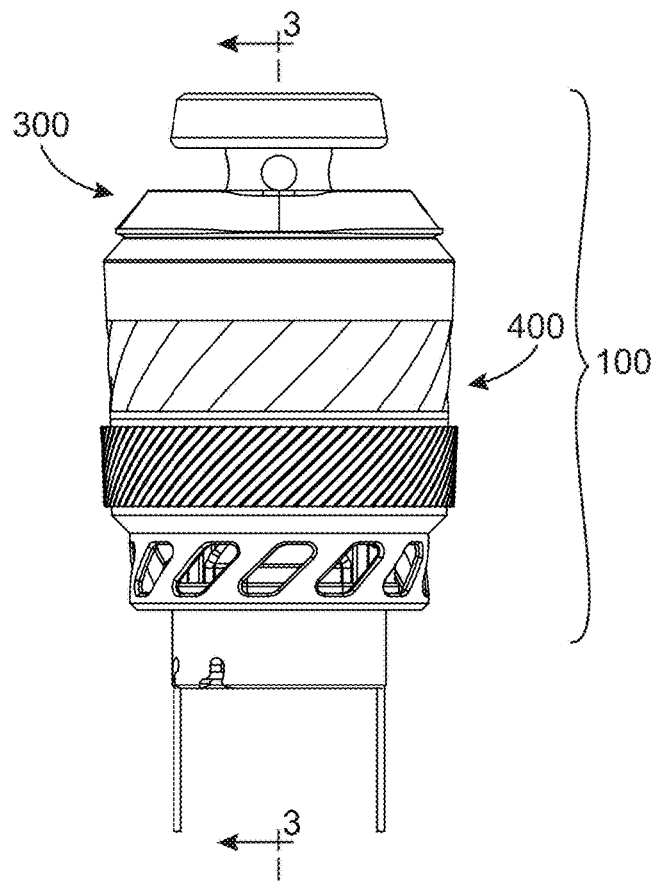
FIG. 2A depicts a front view of an embodiment of a vaporization assembly having a carb cap according to aspects of the present disclosure in a closed configuration.
Figure 2B:
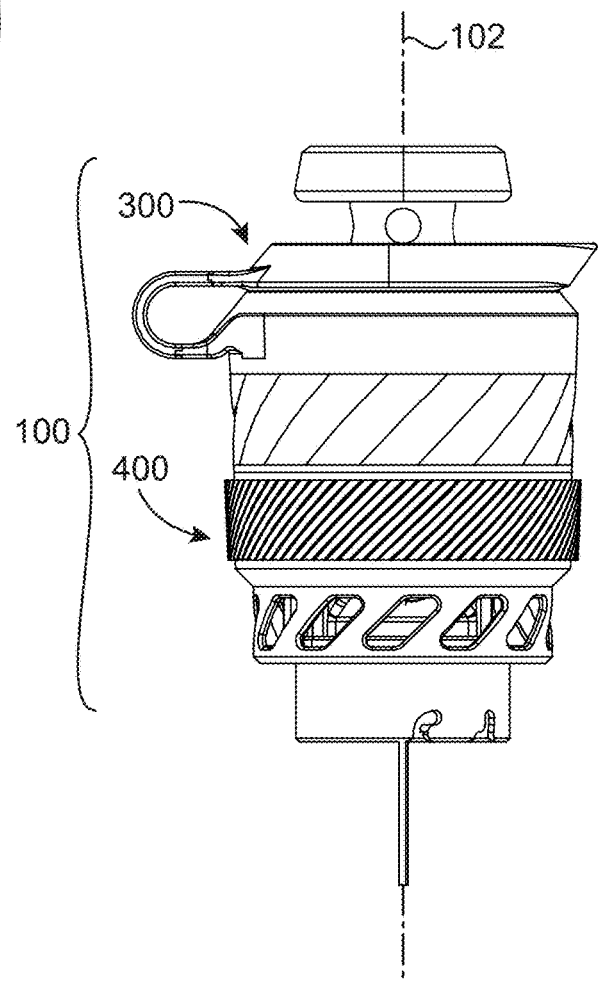
FIG. 2B depicts a side view of an embodiment of a vaporization assembly having a carb cap according to aspects of the present disclosure in a closed configuration.
Figure 3:
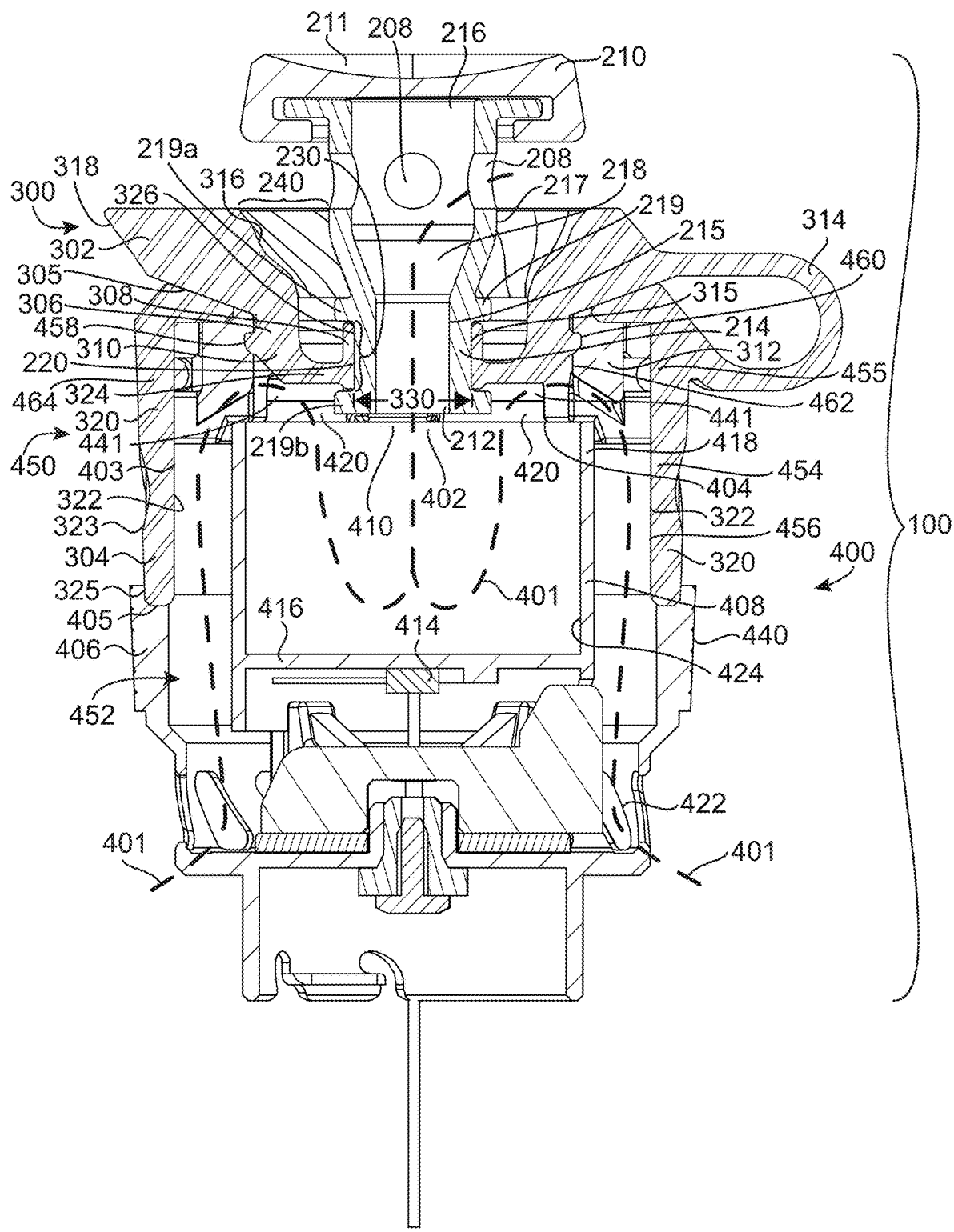
FIG. 3 depicts a cross-section taken along line 3 of FIG. 2A and shows an embodiment of a vaporization assembly having a carb cap according to aspects of the present disclosure.
Figure 10:
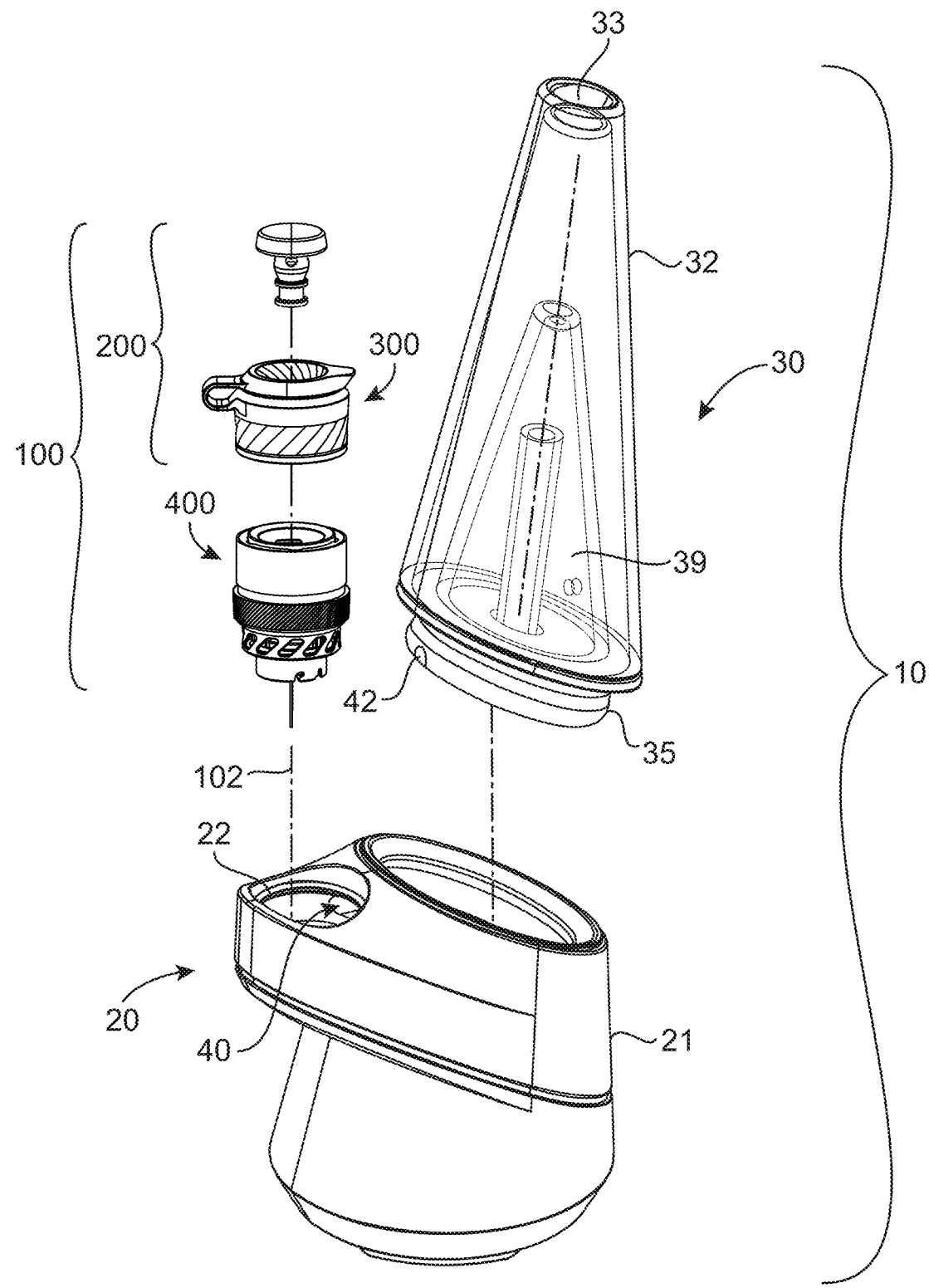
FIG. 10 is an exploded view of one embodiment of a portable vaporization device having a carb cap according to aspects of the present disclosure.
Figure 11:
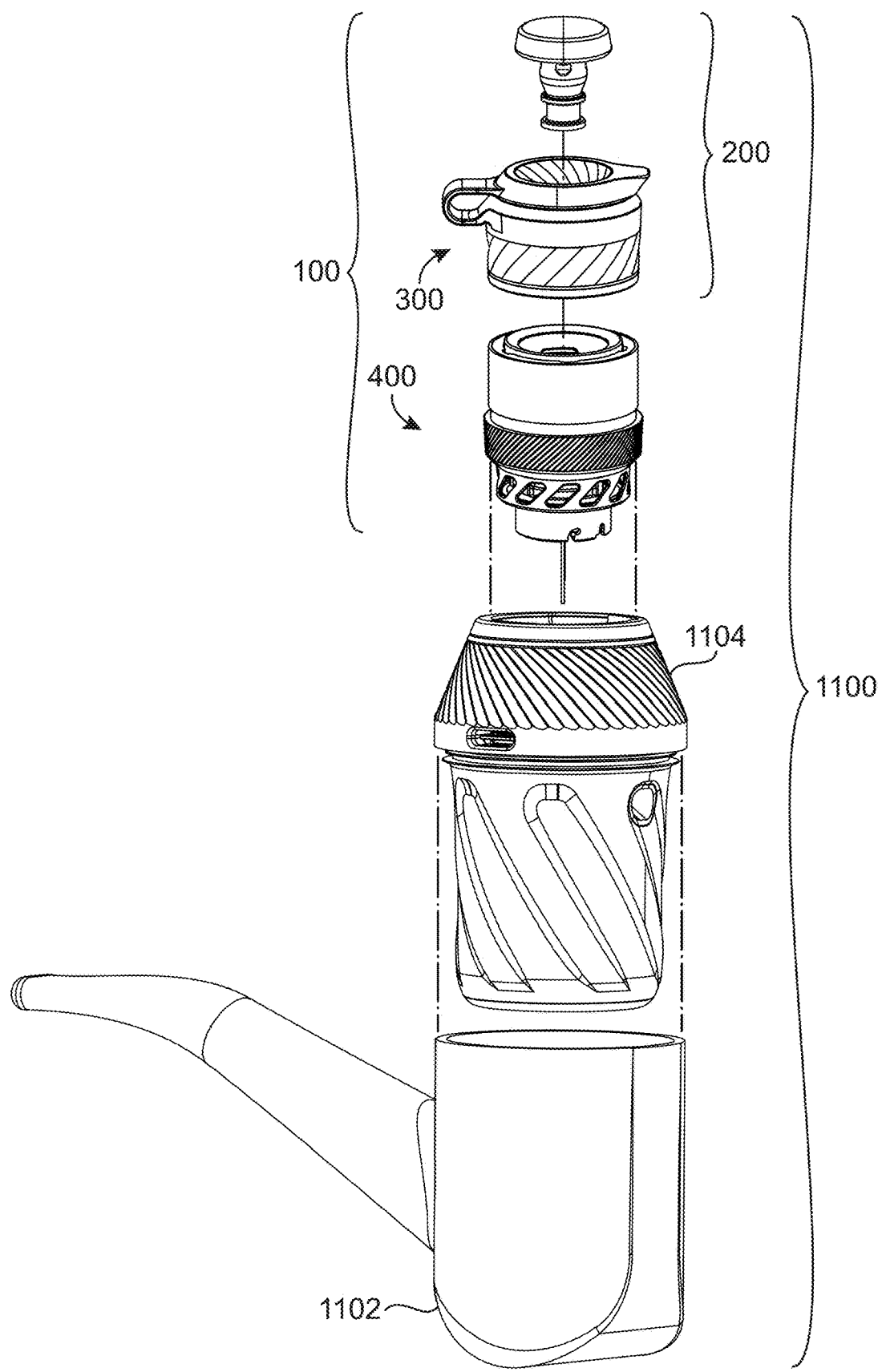
FIG. 11 is an exploded view of one embodiment of another portable vaporization device having a carb cap according to aspects of the present disclosure.

According to aspects of the present disclosure, an embodiment of a carb cap 200 that attaches to a vaporization assembly 400 to form a combined assembly 100, is depicted in FIGS. 1 to 3. The carb cap 200 comprises a vaporization assembly attachment 300, which is configured to attach to a portion of a vaporization assembly 400 that may be used with a portable vaporizing device (e.g., 10 as shown in FIGS. 10 and 1100 as shown in FIG. 11). The carb cap 200 further comprises a movable gas introduction stem 202 with a first end 204 and a second end 206 that is distal to the first end 204. The movable gas introduction stem 202 is configured to introduce gas into the vaporization assembly 400, such as into a container 408 that is configured to hold vaporizable product within the vaporization assembly 400. In certain embodiments, the movable gas introduction stem 202 is movable to allow a directional flow of gas into the vaporization assembly 400 and/or container 408. In one embodiment, the movable gas introduction stem 202 comprises one or more gas inlets 208 located towards the first end 204 of the movable gas introduction stem 202. The one or more gas inlets 208 are configured to introduce gas into the first end 204 of the movable gas introduction stem 202, with the gas being flowed toward the second end 206 of the movable gas introduction stem 202 through a gas flow conduit 218, for example when a user of the device draws and/or inhales from the device, to create a negative gas pressure within the device that pulls a flow of gas from the ambient environment and into the device. The movable gas introduction stem 202 also comprises a gas outlet 212 that introduces gas into the vaporization assembly 400, such as into the container 408. In some embodiments, the one or more gas inlets 208 comprise plurality of gas inlets 208 located toward the first end 204 and are located at a plurality of circumferentially disposed positions about the gas flow conduit 218 of the movable gas introduction stem 202. The one or more gas inlets 208, the gas flow conduit 218, and the gas outlet 212 are in fluid communication with each other to provide a flow of gas into the one or more gas inlets 208, along the gas flow conduit 218, and out of the gas outlet 212.

In one embodiment, the movable gas introduction stem 202 also comprises a cover 210 on the first end 204.

In one embodiment, the carb cap 200 includes a flexible diaphragm 306, for example as depicted in FIG. 3. The flexible diaphragm 306 is configured to extend between the movable gas introduction stem 202 and the vaporization assembly attachment 300 to allow for movement of the movable gas introduction stem 202 with respect to the vaporization assembly attachment 300.

Figure 4A:
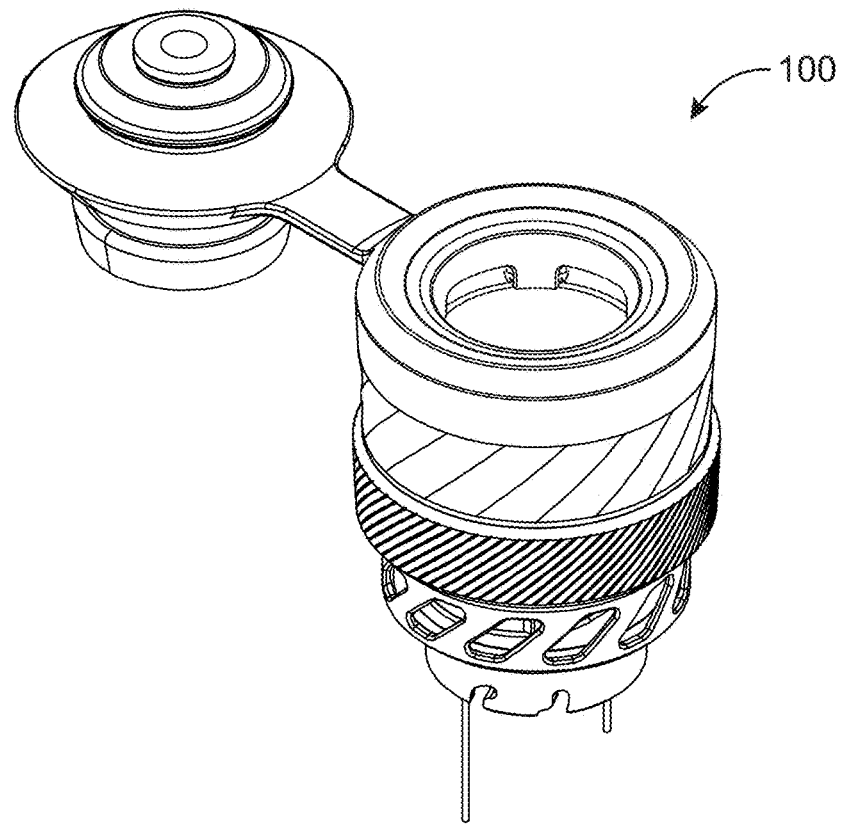
FIG. 4A depicts a top perspective view of an embodiment of a vaporization assembly having a carb cap according to aspects of the present disclosure in an open configuration.
Figure 4B:
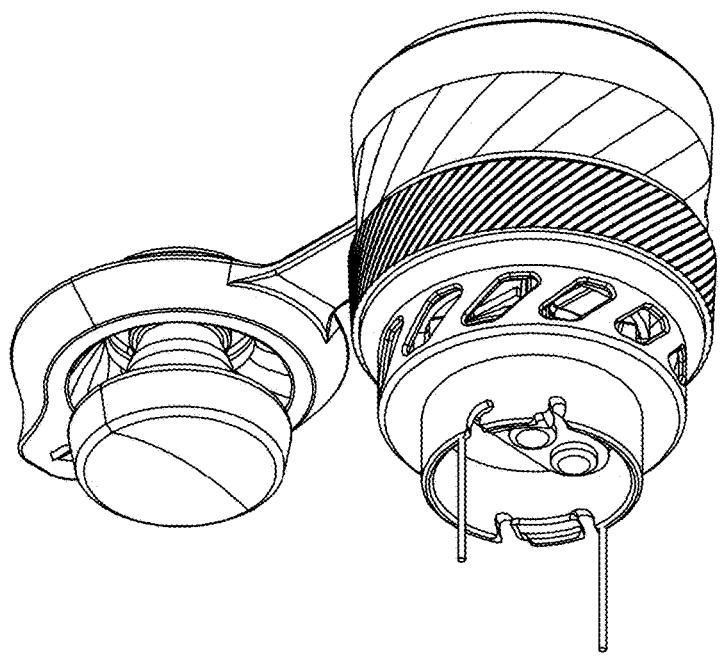
FIG. 4B depicts a bottom perspective view of an embodiment of a vaporization assembly having a carb cap according to aspects of the present disclosure in an open configuration.
Figure 5A:
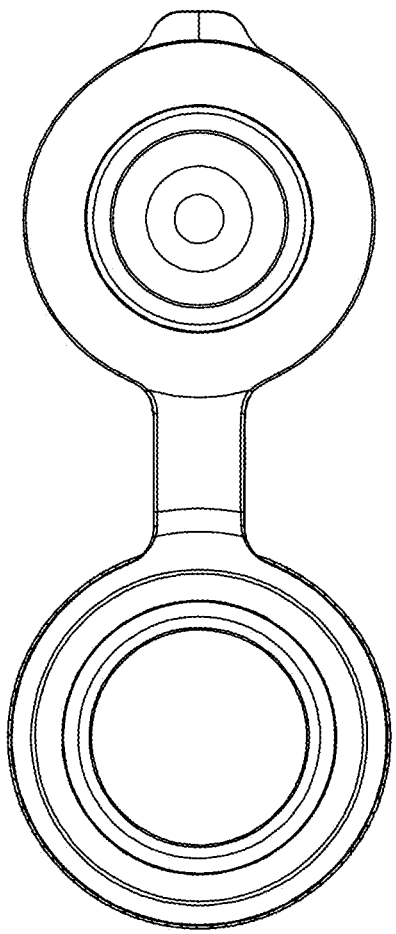
FIG. 5A depicts a top view of an embodiment of a vaporization assembly having a carb cap according to aspects of the present disclosure in an open configuration.
Figure 5B:
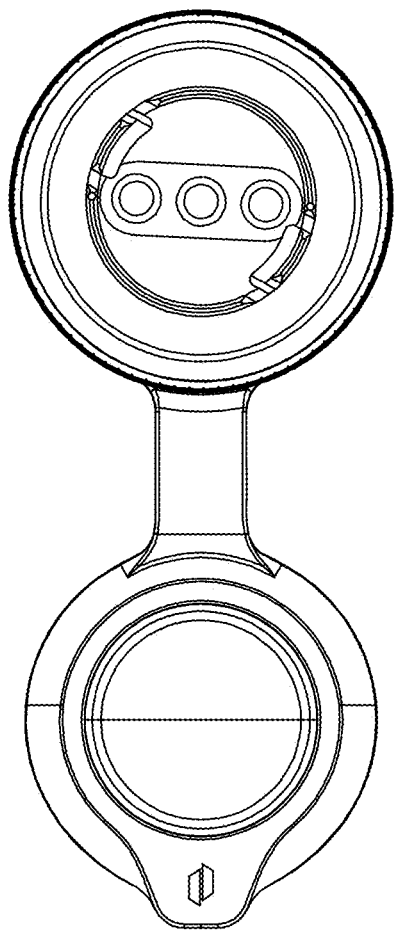
FIG. 5B depicts a bottom view of an embodiment of a vaporization assembly having a carb cap according to aspects of the present disclosure in an open configuration.
Figure 6A:
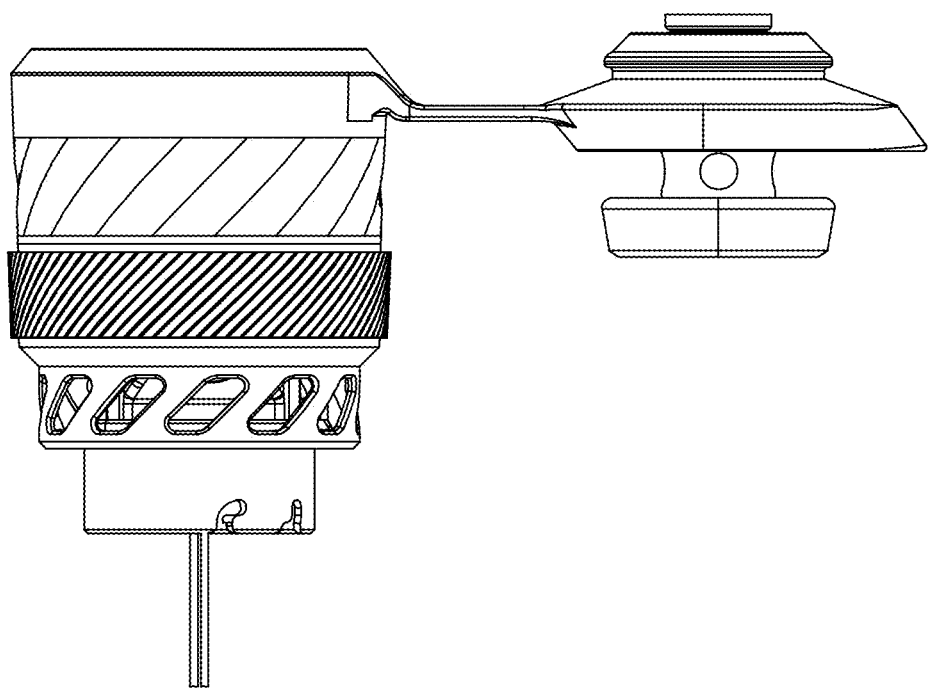
FIG. 6A depicts a side view of an embodiment of a vaporization assembly having a carb cap according to aspects of the present disclosure in an open configuration.
Figure 6B:
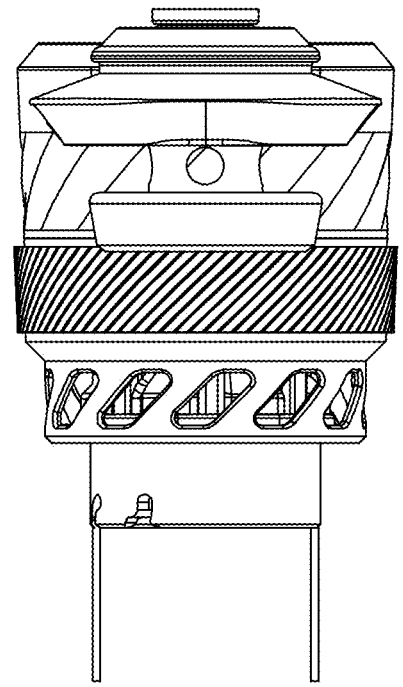
FIG. 6B depicts a back view of an embodiment of a vaporization assembly having a carb cap according to aspects of the present disclosure in an open configuration.
Figure 7A:
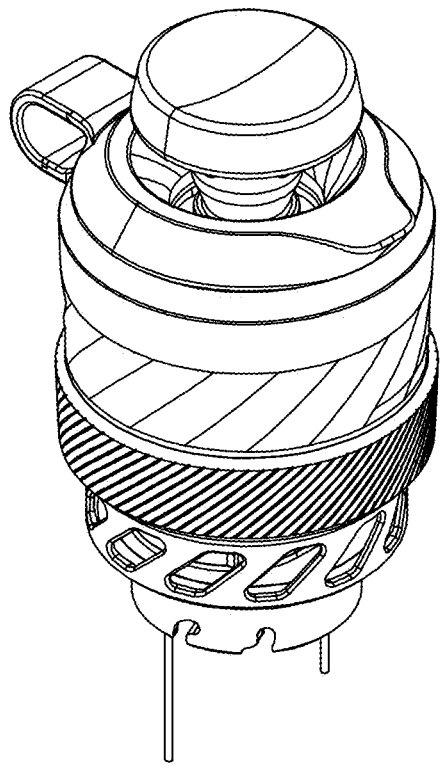
FIG. 7A depicts a top perspective view of an embodiment of a vaporization assembly having a carb cap according to aspects of the present disclosure in a closed configuration.
Figure 7B:
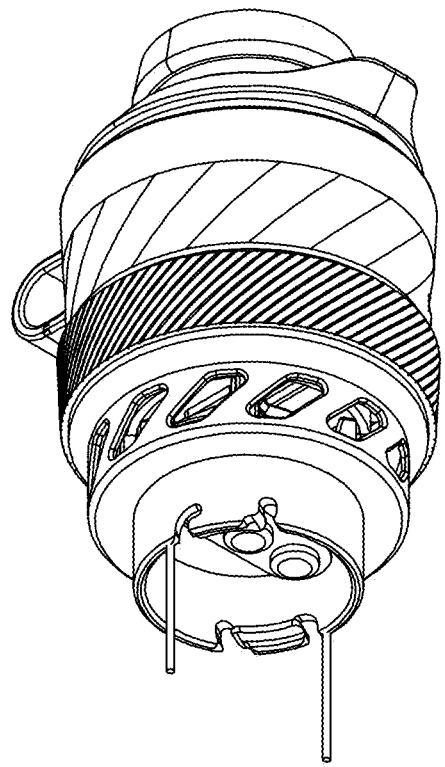
FIG. 7B depicts a bottom perspective view of an embodiment of a vaporization assembly having a carb cap according to aspects of the present disclosure in a closed configuration.
Figure 8A:
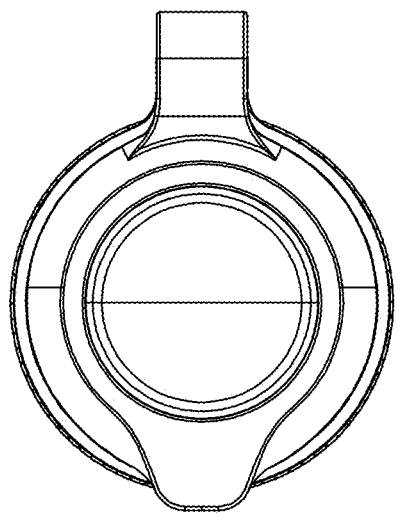
FIG. 8A depicts a top view of an embodiment of a vaporization assembly having a carb cap according to aspects of the present disclosure in a closed configuration.
Figure 8B:
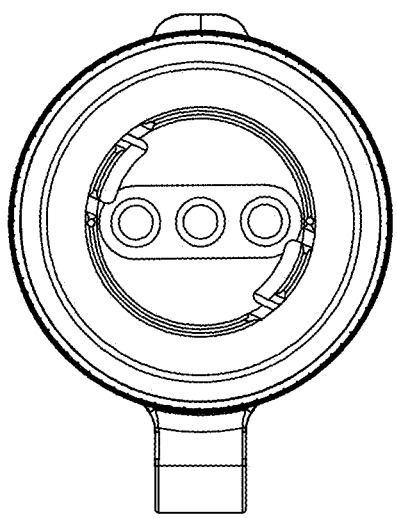
FIG. 8B depicts a bottom view of an embodiment of a vaporization assembly having a carb cap according to aspects of the present disclosure in a closed configuration.

FIGS. 2A and 2B depict an embodiment of a carb cap 200 attached to a vaporization assembly 400, such as via attachment to one or more structures of the vaporization assembly 400, such as a housing or insert structure of the vaporization assembly 400. FIG. 2A and FIG. 2B depict the carb cap 200 in a closed configuration with the vaporization assembly attachment 300 being attached to the vaporization assembly 400. FIGS. 4A and 4B depict the carb cap 200 in an open configuration, with an upper segment 302 of the vaporization assembly attachment 300 removed from and/or opened with respect to a lower segment 304 of the vaporization assembly attachment 300 to allow access to an interior of the vaporization assembly 400, such as the container 408. Referring to FIG. 3, a vertical cross-section running along line 3 from FIG. 2A is shown. FIG. 3 depicts an embodiment of the carb cap 200 in a closed configuration. In some embodiments, the vaporization assembly attachment 300 forms an airtight seal with the vaporization assembly 400 when in the closed configuration.

Referring to FIG. 3, in certain embodiments, the vaporization assembly attachment 300 is configured to be attached to one or more structures 450 of the vaporization assembly 400, including any one or more of an upper wall 454 of the vaporization assembly 400, a portion of a vaporization assembly housing 440, a container 408 configured to hold vaporizable product within the vaporization assembly 400, an annular insert 312 disposed over the container 408, and/or a heating device 414 of the vaporization assembly 400. In some embodiments, the vaporization assembly attachment 300 is configured to be attached to an annular insert 312 disposed over the container 408 that is configured to hold vaporizable product within the vaporization assembly 400. In certain embodiments, at least a portion of the vaporization assembly attachment 300 is configured to extend over the top 455 and outer surface 456 of the vaporization assembly housing 440, such as over the top and outer surface of an upper wall 454 of the vaporization assembly housing 440. In another embodiment, the vaporization assembly attachment 300 comprises an upper segment 302 that is configured to engage the annular insert 312, and a lower segment 304 that is configured to be mounted to an upper wall 454 of the vaporization assembly housing 440. In still another embodiment, the upper segment 302 is removably attachable from, and/or openable with respect to, the lower segment 304, to allow for access to an interior of the vaporization assembly 400 while the lower segment 304 remains mounted on the vaporization assembly housing 440. In one embodiment, the upper and lower segments 302, 304 are optionally connected via a tether 314. In yet another embodiment, the upper segment 302 comprises one or more annular sealing ribs 458 that are configured to engage a complementary channel 460 on an inner wall 462 of the annular insert 312, and the lower segment 304 comprises an annular jacket 464 that surrounds a periphery of the upper wall 454 of the vaporization assembly housing 440.

Figure 9D:
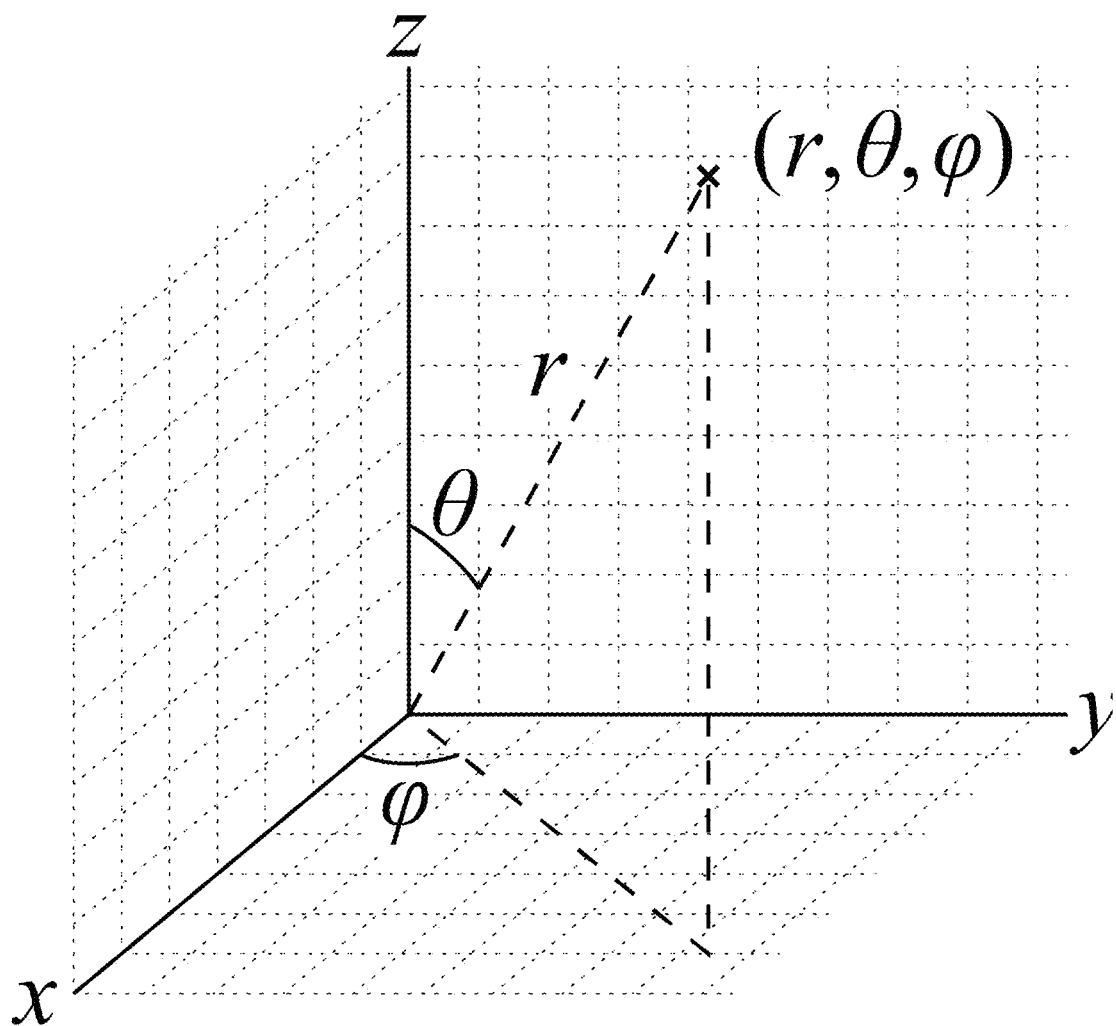
FIG. 9D is a graph showing angles of rotation of the movable gas introduction stem of embodiments of the carb cap of the present disclosure.
Figure 9E:
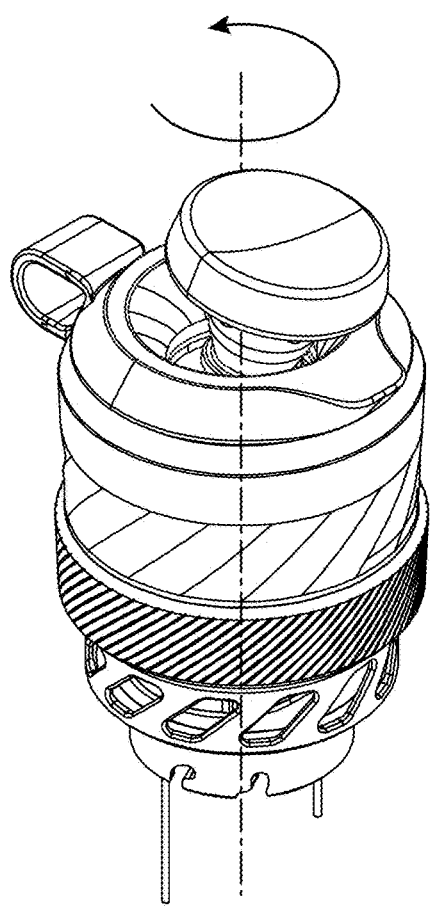
FIG. 9E and FIG. 9F depict an embodiment of a vaporization assembly having a carb cap according to aspects of the present disclosure, showing different angles of rotation (9E, counterclockwise; 9F, clockwise) of the movable gas introduction stem of the carb cap.
Figure 9F:
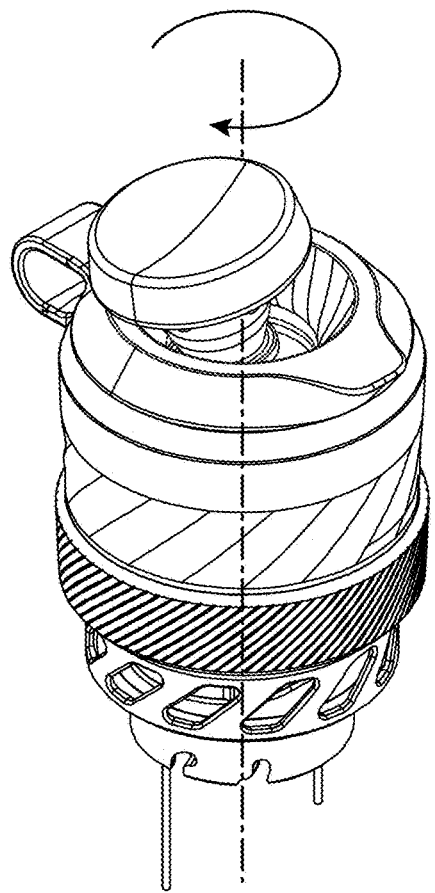

According to certain embodiments, the flexible diaphragm 306 is configured to flex in relation and in response to force applied by a user to the movable gas introduction stem 202, to allow the movable gas introduction stem 202 to move independently of the vaporization assembly attachment 300, such as according to the user's preferences. According to one embodiment, the movable gas introduction stem 202 is rotatable with respect to an imaginary central axis 102 passing through the center of the carb cap 200, in a first direction (e.g. the vertical direction) in response to a force applied by the user to the movable gas introduction stem 202. For example, if the imaginary central axis 102 is understood to be in the vertical direction, in certain embodiments the movable gas introduction stem 202 is capable of being rotated away from this vertical direction (e.g. downwardly), such that the first end 204 of the movable gas introduction stem 202 is displaced from the vertical axis. In some embodiments, a joining region 230 where the movable gas introduction stem 202 meets the flexible diaphragm 306 serves as a pivot point, to allow movement, rotation, tilting and/or deflection of first end 204 of the movable gas introduction stem 202 with respect to the central axis 102. In some embodiments, the degree of movement of the movable gas introduction stem 202 is proportional to the extent of the movement of the flexible diaphragm 306 in response to the force applied 902 by the user as is depicted in FIGS. 9A and 9C. In certain embodiments, the first end 204 of the movable gas introduction stem 202 can be moved and/or tilted away from the central axis 102 in any direction with respect to the central axis 102, such as towards the front, back, or sides of the carb cap 200, or even any direction 360 degrees about the central axis 102. For example, as shown in FIGS. 9D and 9E, if the central axis 102 is understood to correspond to a z axis in a spherical coordinate system having a polar angle (theta, θ) with respect to the z axis, and azimuthal angle (phi, φ) with respect to an initial meridian plane, the first end 204 of the movable gas introduction stem 202 may in certain embodiments be moved and/or tilted away from the central axis 102 by any desired angle θ (e.g. downwardly), and at an angle q that is selected from any of the angles 360 degree about the z axis (e.g. towards the front, sides, back, etc. of the carb cap). That is, according to certain embodiments, the movable gas introduction stem 202 can be understood as being capable of both being rotated downwardly with respect to the vertical axis (θ), as well as in any direction 360 degrees about the vertical axis (φ). By allowing movement of the movable gas introduction stem 202 with respect to the central axis 102, a direction and angle of gas introduced into the vaporization assembly 400 can be controlled. In some embodiments, the movable gas introduction stem 202 may be capable of being rotated away from the central axis 102 (e.g., in the downward direction, or through θ angle) by at least 5, at least 10, at least 15, at least 20, at least 30, and/or at least 45 degrees. For example, in some embodiments, the movable gas introduction stem 202 may be capable of being tilted radially away from the central axis 102. In some embodiments the movable gas introduction stem 202 is configured to be tilted away from the central axis 102 (e.g., downwardly, or through a θ angle) by at least 5, at least 10, at least 15, at least 20, at least 30, and/or at least 45 degrees. As another example, in some embodiments, the movable gas introduction stem 202 is configured to be deflected away from a central axis 102 passing through the carb cap 200 in a first direction, in response to a force applied by the user to the movable gas introduction stem 202. In some embodiments, the movable gas introduction stem 202 is deflected away from the central axis 102 (e.g., downwardly, or through a θ angle) by at least 5, at least 10, at least 15, at least 20, at least 30, and/or at least 45 degrees.

In certain embodiments, the movable gas introduction stem 202 is biased towards the vertical direction, such that a release of the force applied by a user results in the movable gas introduction stem 202 returning to a position where it is aligned along the vertical direction. In some embodiments, the second end 206 of the movable gas introduction stem 202 may extend into the container 408 but shall not touch the walls or bottom of the container 408 when rotated downwardly and/or tilted away from the central axis 102.

In some embodiments, the vaporization assembly attachment 300 has an outer edge 318 and an inner edge 316, wherein the inner edge 316 is radially interior to the outer edge 318. In some embodiments, a degree to which the movable gas introduction stem 202 can be tilted radially away from the central axis 102 is limited by contact with the inner edge 316 of the vaporization assembly attachment 300. For example, the inner edge 316 may be positioned to block or inhibit further deflection of the movable gas introduction stem 202 by contact therewith. The inner edge 316 of the vaporization assembly attachment 300 may also be configured to provide a gap 240 between the inner edge 316 and the movable gas introduction stem 202 that provides for a sufficient degree of movement of the movable gas introduction stem 202 with respect to the central axis 102 to provide for control of the direction and/or angle of gas introduced into the vaporization assembly 400 by the movable gas introduction stem 202.

In some embodiments, the flexible diaphragm 306 and the vaporization assembly attachment 300 form a single piece. For example, the flexible diaphragm 306 and vaporization assembly attachment 300 may form a single unitary structure that is capable of attaching to a vaporization assembly device and also providing the flex and/or rotation of the movable gas introduction stem 202 via flexing of the flexible diaphragm 306. In some embodiments, the flexible diaphragm 306 and the vaporization assembly attachment 300 are separate pieces, and/or are configured to be removably attached to each other. In some embodiments, the movable gas introduction stem 202 is a separate piece from the flexible diaphragm 306, for example, the flexible diaphragm 306 may be configured to be connected to the movable gas introduction stem 202. In some embodiments, the movable gas introduction stem 202 and the flexible diaphragm 306 are one piece, and/or may form a single unitary structure. In some embodiments, the movable gas introduction stem 202 is removably attachable to the flexible diaphragm 306. For example, in certain embodiments, the movable gas introduction stem 202 and/or the vaporization assembly attachment 300 may be formed of a more rigid material that is attached and/or connected to a more flexible material that makes up the flexible diaphragm 306. Furthermore, according to certain embodiments, the movable gas introduction stem 202 may be removed from the flexible diaphragm 306, for example, to allow for cleaning of the carb cap components. According one embodiment, the flexible diaphragm 306 is made from an elastomeric or other flexible material, such as for example a flexible silicone material, whereas the movable gas introduction stem 202 may be formed of a stiffer material, such as for example a stiffer plastic, a metal or a ceramic. The vaporization assembly attachment 300 may also be formed of a stiffer material, such as a stiffer plastic, or may be formed of the same or similar elastomer as the flexible diaphragm 306 and with a thickness that provides greater structural rigidity than the flexible diaphragm 306. In some embodiments, the vaporization assembly attachment 300, the flexible diaphragm 306, and the movable gas introduction stem 202 together form a single piece.

As is depicted in FIG. 3, in some embodiments the movable gas introduction stem 202 further comprises a cover 210 configured to at least partly cover the first end 204 of the movable gas introduction stem 202. In some embodiments, the cover 210 is made of an elastomeric material. In some embodiments, the cover 210 comprises silicone. In some embodiments, the cover 210 and the moveable gas introduction stem 202 are one piece.

In some embodiments, the movable gas introduction stem 202 has a central stem aperture 216 open at the first end 204 and one or more gas inlets 208 between the first end 204 and the second end 206. In some embodiments, the cover 210 is configured to cover and seal closed the central stem aperture 216 such that the seal is airtight. In some embodiments, the cover 210 also comprises a handle 211 for a user to control the movable gas introduction stem 202.

In some embodiments, the carb cap 200 is used in conjunction with a vaporization assembly housing 440 that is configured to house a vaporizable product container 408 as depicted in FIG. 3. The vaporization assembly housing 440 also includes a vaporization assembly housing inlet 441 configured to introduce gas into the vaporization assembly housing 440. In some embodiments, the vaporizable product container 408 includes a vaporizable product container inlet 410 which is configured to be aligned and in communication with the vaporization assembly housing inlet 441.

The vaporization assembly 400 also includes a vaporization assembly housing outlet 422 configured to exhaust gas from the vaporization assembly 400. In some embodiments, the vaporization assembly 400 includes a heating device 414 to heat vaporizable product (not depicted) into vapor, when the vaporizable product is in the vaporizable product container 408. In some embodiments, the vaporizable product container 408 comprises one or more container walls 424, and may comprise one or more container outlets 420 to exhaust vaporizable product from the container 408. In some embodiments, the carb cap 200 including the vaporization assembly attachment 300 and the movable gas introduction stem 202 is positioned over a vaporization assembly inlet 402 at the top end 404 of the vaporization assembly housing 440. In one embodiment, the vaporization assembly 400 comprises one or more vaporization assembly housing walls 406 that at least partially define a vaporization assembly internal flow path 401.

In some embodiments, the vaporization assembly 400 also comprises a vaporizable product container 408 within the vaporization assembly housing 440. The vaporizable product container 408 is configured to hold vaporizable product (not depicted) therein.

According to certain embodiments, the vaporization assembly 400 also comprises a heating device 414, such as a resistive heating element or resistive heating trace, in contact with the bottom end 416 of the vaporizable product container 408. In certain embodiment, the heating device 414 can also comprise a heating plate, heating rod, or other structure having resistive heating elements and/or heating traces that are capable of conductively heating of the container 408. In other embodiments, the heating device 414 may comprise an inductively heating device capable of inductively heating the container 408, and/or may be capable of radiatively heating the vaporizable product container 408 and/or vaporizable product within the container 408. In some embodiments, the heating device 414 comprises a ceramic heating plate, such as an alumina plate, that is capable of being heated by a resistive heating element and/or heating trace, and may also comprise, e.g., a metal wire, coil, trace, or other element that is capable of resistively heating, and which may also be embedded in a ceramic or glass heating plate or used alone. In some embodiments, the vaporization assembly 400 also comprises an annular insert 312 that thermally insulates the top end 418 of the vaporizable product container 408 from the vaporization assembly housing 440.

In some embodiments, the one or more vaporizable product container walls 424 of the vaporizable product container 408 can comprise a resistive heating element (not depicted) such as heater traces embedded therein that form the heating device 414 to heat the vaporizable product held in the container 408, e.g., by wrapping the heating element with soft ceramic material and forming a tube shape, adhering a thin ceramic bottom (without traces) to the tube, then firing the soft ceramic with heating element embedded therein to obtain the vaporizable product container 408. In another embodiment, the bottom end 416 of the vaporizable product container 408 may also comprise heating element (heater traces) embedded therein. In some embodiments, the heating device 414 is attached to conductive elements such as wires leading to the power source (e.g., a battery).

Additional embodiments of heating device, heating elements, heating plates and any other heating structures that can be used to form all or part of the heating device 414 have been described in U.S. Pat. Nos. 10,517,334 and 11,375,752, which is hereby incorporated by reference herein in its entirety.

In some embodiments, the flexible diaphragm 306 of the vaporization assembly attachment 300 is configured to extend radially inwardly over the vaporization assembly inlet 402 at the top end 404 of the vaporization assembly 400 when the vaporization assembly attachment 300 is attached to the vaporization assembly 400.

In some embodiments, the movable gas introduction stem 202 has a radially exterior wall 215, and where the radially exterior wall 215 includes a sealing region 214 formed about a circumference of the exterior wall 215 of the movable gas introduction stem 202. In some embodiments, the movable gas introduction stem 202 sealing region 214 is configured to retain the movable gas introduction stem 202 as received by the flexible diaphragm 306, when the movable gas introduction stem 202 is attached to the flexible diaphragm 306. In some embodiments, the sealing region 214 on the radially exterior wall 215 comprises upper and lower sealing region ridges 219a, 219b that engage and retain the flexible arm 308 of the flexible diaphragm 306 therebetween. In some embodiments, the sealing region 214 extends entirely about a circumference of the radially exterior wall 215. In some embodiments, the sealing region 214 also contains one or more sealing region ridges 219 configured to engage and retain the flexible diaphragm 306. For example, the sealing region ridges 219 may form annular ribs surrounding the circumference of the radially exterior wall and defining the upper and lower bounds of the sealing region, such as with upper and lower sealing region ridges 219a, 219b, to retain the flexible diaphragm in an engaged relationship with the sealing region 214.

In some embodiments, the flexible diaphragm 306 has a flexible arm 308 depicted in FIG. 3, at a radially interior end 315 of the flexible diaphragm 306. The flexible arm 308 comprises one or more sealing surfaces 326 configured to provide an airtight seal with the movable gas introduction stem sealing region 214 when the movable gas introduction stem 202 is attached to the flexible diaphragm 306. In some embodiments, the movable gas introduction stem 202 is configured to be removably attachable to the flexible diaphragm 306. In some embodiments, the removably attachable movable gas introduction stem 202 is configured to be removed from attachment with the flexible diaphragm 306 by pulling outwardly with a force that exceeds a retaining force of the sealing region 214 with the one or more sealing surfaces 326 of the flexible arm 308.

In some embodiments, when the movable gas introduction stem 202 is detached from the vaporization assembly attachment 300, the movable gas introduction stem 202 is configured to be attached to the flexible diaphragm 306 by pushing the movable gas introduction stem 202 inwardly through a central aperture 330 of the flexible diaphragm 306 with a force that exceeds a resistive force of the sealing region ridges 219 to engage the sealing region 214 of the movable gas introduction stem 202 with the sealing surfaces of the flexible diaphragm 306. The movable gas introduction stem 202 is attached to the flexible diaphragm 306 when the one or more sealing surfaces 326 of the flexible arm 308 of the flexible diaphragm 306 form an airtight seal with the sealing region 214 of the movable gas introduction stem 202, e.g., when the sealing surfaces 326 of the flexible arm 308 are engaged with the sealing region 214 and retained between the sealing region ridges 219. In some embodiments, the sealing region 214 is located toward the second end 206 of the movable gas introduction stem 202 on the exterior wall 215 of the movable gas introduction stem 202.

In some embodiments, when the movable gas introduction stem 202 is attached to the flexible diaphragm 306, movement of the movable gas introduction stem 202 with respect to the flexible diaphragm 306 does not break the airtight seal between the sealing surfaces 326 of the flexible arm 308 and the sealing region 214 of the movable gas introduction stem 202. For example, the flexible arm 308 of the flexible diaphragm 306 may be capable of bending and extending in response to movement of the movable gas introduction stem 202 at a flexible joint 324 between the flexible arm 308 and the main body 310 of the flexible diaphragm 306, as shown for example in FIGS. 9A-9C. The main body 310 of the flexible diaphragm 306 is also, in certain embodiments, capable of flexing and/or bending in response to movement of the movable gas introduction stem 202 in a manner that maintains the seal between the flexible arm 308 and the sealing region 214 of the movable gas introduction stem 202. In some embodiments, there is substantially no translation between surface 220 of the sealing region 214 of the movable gas introduction stem 202 and the sealing surfaces 326 of the flexible arm 308 when the movable gas introduction stem 202 is moved in response to a force 902 being applied. That is, in certain embodiments, the sealing surfaces 326 of the flexible arm 308 stay substantially in place with respect to the sealing region 214 of the movable gas introduction stem 202, even when the movable gas introduction stem 202 is being rotated or moved by a user, substantially without slipping or moving along the sealing region 214 of the moveable gas introduction stem 202, to maintain an airtight seal with the moveable gas introduction stem 202.

FIGS. 9A-9C show that, in some embodiments the flexible arm 308 of the flexible diaphragm 306 forms a flexible joint 324 with a main body 310 of the flexible diaphragm 306, which allows the flexible diaphragm 306 to bend and flex with respect to the moveable gas introduction stem 202, which maintaining a seal thereto via the flexible arm 308. For example, referring to FIG. 9B, in certain embodiments, the one or more sealing surfaces 326 of the flexible arm 308 of the flexible diaphragm 306 are substantially parallel with the sealing region 214 of the movable gas introduction stem 202, and the one or more sealing surfaces 326 of the flexible arm 308 are substantially perpendicular to the main body 310 of the flexible diaphragm 306, when the movable gas introduction stem 202 is aligned along the central axis 102. As shown in FIGS. 9A and 9C, the movement of the moveable gas introduction stem 202 results in bending and/or flexing of the flexible diaphragm 306, such as at the joint and along the body of the flexible diaphragm 306, such that while the one or more sealing surfaces 326 of the flexible arm 308 remain substantially parallel to the sealing region 214 of the movable gas introduction stem 202, the sealing surfaces 326 of the flexible arm 308 are bent towards and/or away from the main body 310 of the flexible diaphragm 306.

In some embodiments, the flexible diaphragm 306 comprises a central aperture 330 configured to receive the movable gas introduction stem 202. The flexible diaphragm 306 comprises a flexible diaphragm flexible arm 308 at the radially interior end 315 of the flexible diaphragm 306 and about a perimeter of the central aperture 330. In some embodiments, a vertical cross-section of the flexible diaphragm 306 is thinner than the vertical cross-section of the vaporization assembly attachment 300, to provide enhanced flexibility of the flexible diaphragm 306 as compared to the vaporization assembly attachment 300. In some embodiments, the vertical cross-section thickness of the flexible diaphragm 306 is tapered radially inward so that the radially interior end 315 is thinner than a radially exterior end of the flexible diaphragm 306, such as for example at a region about the joint between the flexible arm 308 and main body 310 of the flexible diaphragm 306.

In some embodiments, the flexible diaphragm 306 is biased to return the movable gas introduction stem 202 to a resting position, as depicted in FIG. 9B, that is aligned with the central axis 102 when no force is being applied by the user. As is depicted in FIGS. 9A through 9C, the force applied 902 on the movable gas introduction stem 202 changes the orientation of the flow of gas 904 into the vaporizable product container 408. For example, in the embodiment as shown in FIG. 9B, no force is being applied to the movable gas introduction stem 202, and so it resides in its resting position aligned with the central axis 102. In FIG. 9B, gas entering the movable gas introduction stem 202 is introduced in a vertical direction towards a central region 425 of the container 408. In FIGS. 9A and 9C, a force 902 is applied to rotate the movable gas introduction stem 202 away from the central axis 102 (away from vertical), such that gas entering the movable gas introduction stem 202 is introduced at an angle into the container 408, such as towards a side region 426 of the container 408. The angle of rotation of the movable gas introduction stem 202 can be selected to provide for introduction of the gas at regions of the container 408 that are desired by the user of the device, to enhance the vaporization of the product. Furthermore, as discussed above while the rotation depicted in FIGS. 9A and 9C is in a plane of the page (to the left and to the right), embodiments of the carb cap 200 are not limited to this movement, and the movable gas introduction stem 202 may be capable of rotating downwardly in any direction (360 degrees) about the central axis 102 (e.g. in spherical polar coordinates, at any q angle about the central axis, and in a predetermined θ angle downwardly away from the central axis), to provide for directional introduction of gas into the container 408 at a desired angle with respect to the central axis 102.

In some embodiments, when a portable electronic vaporizing device is in operation and the vaporization assembly attachment 300 is attached to the vaporization assembly 400, the direction of gas 904 flowing out of the gas outlet 212 of the movable gas introduction stem 202 into the vaporization assembly 400 and into the vaporizable product container 408, is controlled by the movement of the movable gas introduction stem 202 in response to the force 902 applied by the user.

In some embodiments, the gas flow conduit 218 running through the movable gas introduction stem 202 has a Venturi-type shape. For example, in some embodiments, the gas flow conduit 218 is wider toward the first end 204 of the movable gas introduction stem 202 than at the second end 206 of the movable gas introduction stem 202. In some embodiments, the gas flow conduit 218 has a first volume adjacent to the one or more gas inlets 208 at the first end 204 of the movable gas introduction stem 202 and a second volume adjacent the gas outlet 212 and located towards the second end 206 of the movable gas introduction stem 202, wherein the first volume is larger than the second volume. The Venturi-type shape may, in certain embodiments, provide for an acceleration of the gas flowing through the movable gas introduction stem 202. For example, in some embodiments, the velocity of gas flowing through the gas flow conduit 218 increases from the first end 204 to the second end 206 of the movable gas introduction stem 202, when the movable gas introduction stem 202 is attached to the vaporization assembly attachment 300 and the portable electronic vaporizing device is in operation.

According to certain embodiments, the vaporization assembly attachment 300 can be attached to a vaporization assembly 400 by a variety of different mechanisms. In some embodiments, the vaporization assembly attachment 300 comprises a jacket 320 that attaches to the walls 406 of the vaporization assembly housing 440. The jacket 320 comprises an outer wall 323 that extends over an outer surface 403 of the vaporization assembly housing 440 and an inner wall 325 that engages an inner surface 405 of the housing, such that the jacket 320 can be fitted over the top end 404 of the housing 440. In some embodiments, the vaporization assembly attachment 300 comprises sealing surfaces 322 about a periphery thereof that seal to the walls 406 of the vaporization assembly housing 440.

In some embodiments, the vaporization assembly attachment 300 is removably attachable to the vaporization assembly 400. In some embodiments, the vaporization assembly attachment 300 comprises an upper segment 302 and a lower segment 304, wherein the upper segment 302 is configured to attach to the movable gas introduction stem 202 and the lower segment 304 is configured to attach to the vaporization assembly 400. In some embodiments, the vaporization assembly attachment upper segment 302 and the vaporization assembly attachment lower segment 304 are two separate pieces. In some embodiments, a tether 314 connects the vaporization assembly attachment upper segment 302 and lower segment 304, such that the lower segment 304 is configured to maintain attachment to the vaporization assembly 400 even when the upper segment 302 is not attached to the lower segment 304. In certain embodiments, the upper segment 302 is attached to the flexible diaphragm 306 and movable gas introduction stem 202, and rests on an upper surface 305 of the lower segment 304. According to one embodiment, the upper segment 302 can be removed from the lower segment 304, such as by lifting the upper segment 302 off of the lower segment 304. The upper segment 302 may be removed from the lower segment 304, for example, to allow for access to the container 408 within a portable vaporization device, when the carb cap 200 is attached to vaporization assembly housing 440 of such device. After the container 408 has been accessed, the upper segment 302 can be easily reattached to the lower segment 304 to cap the vaporization assembly housing 400.

In some embodiments, the movable gas introduction stem cover 210 has a handle 211 that is configured to be a concave depression to fit a tip of a finger of the user. In some embodiments, the movable gas introduction stem cover 210 has a handle 211 that is configured to be a rounded convex protrusion to fit a tip of a finger of the user.

Referring to FIG. 10, one embodiment of a portable electronic vaporizing device that can be used with the carb cap 200 having the flexible diaphragm 306. In some embodiments, the portable electronic vaporizing device 10 includes a base 20, a mouthpiece 30, and a vaporization assembly 400 comprising a carb cap 200 (to form a combined assembly 100). The portable electronic vaporizing device 10 comprises a removably attachable vaporization assembly 400 and a mouthpiece 30. The removably attachable vaporization assembly 400 is configured to receive a vaporizable product therein and to heat the vaporizable product to form a vapor therefrom. The mouthpiece 30 comprises an inhalation outlet 33 where a user can inhale the vapor produced by the removably attachable vaporization assembly 400, optionally with water or other substances entrained therein. The mouthpiece 30 can be provided in various forms including but not limited to a pipe, or other forms, and optionally can include water filtration. According to one embodiment, the mouthpiece 30 comprises a convoluted internal flow path from a mouthpiece inlet 42 to the inhalation outlet 33, the mouthpiece 30 comprising a first chamber 39 that is internal to a second chamber 32 that at least partially circumferentially surrounds the first chamber 39, and wherein the flow of gas along the mouthpiece internal flow path is received in the at least one mouthpiece inlet 42, passes through the first chamber 39 and into the second chamber 32, and out of the inhalation outlet 33. A conduit 40 formed through the base portion 20 provides a gas flow pathway from the vaporization assembly 400 to the mouthpiece 30.

In some embodiments, the base portion 20 can also comprise a housing 21 for one or more components for powering and/or controlling the portable electronic vaporizing device 10. For example, the base portion 20 may contain compartments therein for storing a power source, such as a battery, for powering elements of the portable electronic vaporizing device 10 such as a heating element or other heating device used in the vaporization assembly 400. According to one embodiment, the flow of gas through the vaporization assembly 400 comprises flow through a container inlet 410 into a top of the container 408, flow out of the container 408 through the container outlets 420 that are separate from the container inlet 410 and disposed towards a top end 404 of the vaporization assembly 400. According to certain embodiments, the vaporization assembly housing 440 at least partially directs gas from the one or more container gas outlets 420 along the internal vaporization assembly gas flow path 452, in a passage formed between walls of the container 408 and the vaporization assembly housing 440. In some embodiments, the vaporization assembly housing further comprises one or more vaporization assembly housing outlets 422 to flow gas from the internal vaporization assembly gas flow path to the conduit 40 formed in the base 20, with the conduit 40 providing a gas flow path from the vaporization assembly 400 to the mouthpiece 30.

In some embodiments, the vaporization assembly 400 is removable from the base 20 independently of removal of the mouthpiece 30. In one embodiment, the mouthpiece 30 is removably attachable to the base portion 20, for example to allow a user to readily remove the mouthpiece 30 for cleaning and/or replacement. For example, according to one embodiment, the base portion 20 and mouthpiece 30 can be removed from one another by exerting a force on the base portion 20 that exceeds a retaining force of sealing regions (described below) that form a seal between portions of the base portion and the mouthpiece), to lift the base portion 20 out of the mouthpiece 30. The base portion 20 can be re-attached to the mouthpiece 30 by inserting the insert portion (described below) into the receiving area 35 of the mouthpiece 30 and engaging the sealing regions to retain the base portion 20 as inserted within the mouthpiece 30. Other mechanisms for removably attaching the base portion 20 to the mouthpiece 30 can also be provided.

In yet another embodiment, the vaporization assembly 400 may be removably attachable to the base portion 20, for example so as to allow a user to replace the vaporization assembly 400 when no longer serviceable, for cleaning of the vaporization assembly 400, and/or to more readily allow access to a vaporizable product container 408 (e.g. bowl) where a vaporizable product may be loaded into the vaporization assembly 400. For example, the vaporization assembly may be received in a vaporization assembly receiving area 22 of the base portion 20, and can be attached to the base portion 20 by twisting to engage and secure the vaporization assembly 400 in the receiving area 22. The vaporization assembly 400 can be removed by untwisting to release from the receiving area 22 of the base portion 20. Other mechanisms for removably attaching the vaporization assembly 400 to the base portion 20 can also be provided. In one embodiment, both the vaporization assembly 400 and the mouthpiece 30 may be removably attachable to the base portion 20. In yet another version, the vaporization assembly 400 may be independently removable from the base portion 20. That is, the vaporization assembly 400 may be configured to be removably attached to the base portion 20 such that it can be removed therefrom, without requiring that the mouthpiece 30 and/or base portion 20 be removed from one another beforehand.

In yet another embodiment, the vaporization assembly 400 comprises the heating device 414, that may be provided separately and/or as a part of the vaporizable product container 408 in any suitable form. For example, the heating device 414 may comprise at least one of a heating plate, a heating ring, and a heating element, for example comprising one or more resistively heating traces, and is capable of conductively heating the vaporizable product in the vaporizable product container 408. For example, the heating device 414 can comprise one or more heating resistively heating traces embedded in the walls of the container 408, that conductively heat vaporizable product in the container 408.

In certain embodiments, one or more airtight seals are formed between the base portion 20 and/or the vaporization assembly 400 and the mouthpiece 30, to create an airtight gas flow path from the vaporization assembly 400, through the base portion 20, and to the mouthpiece 30.

Figure 12A:
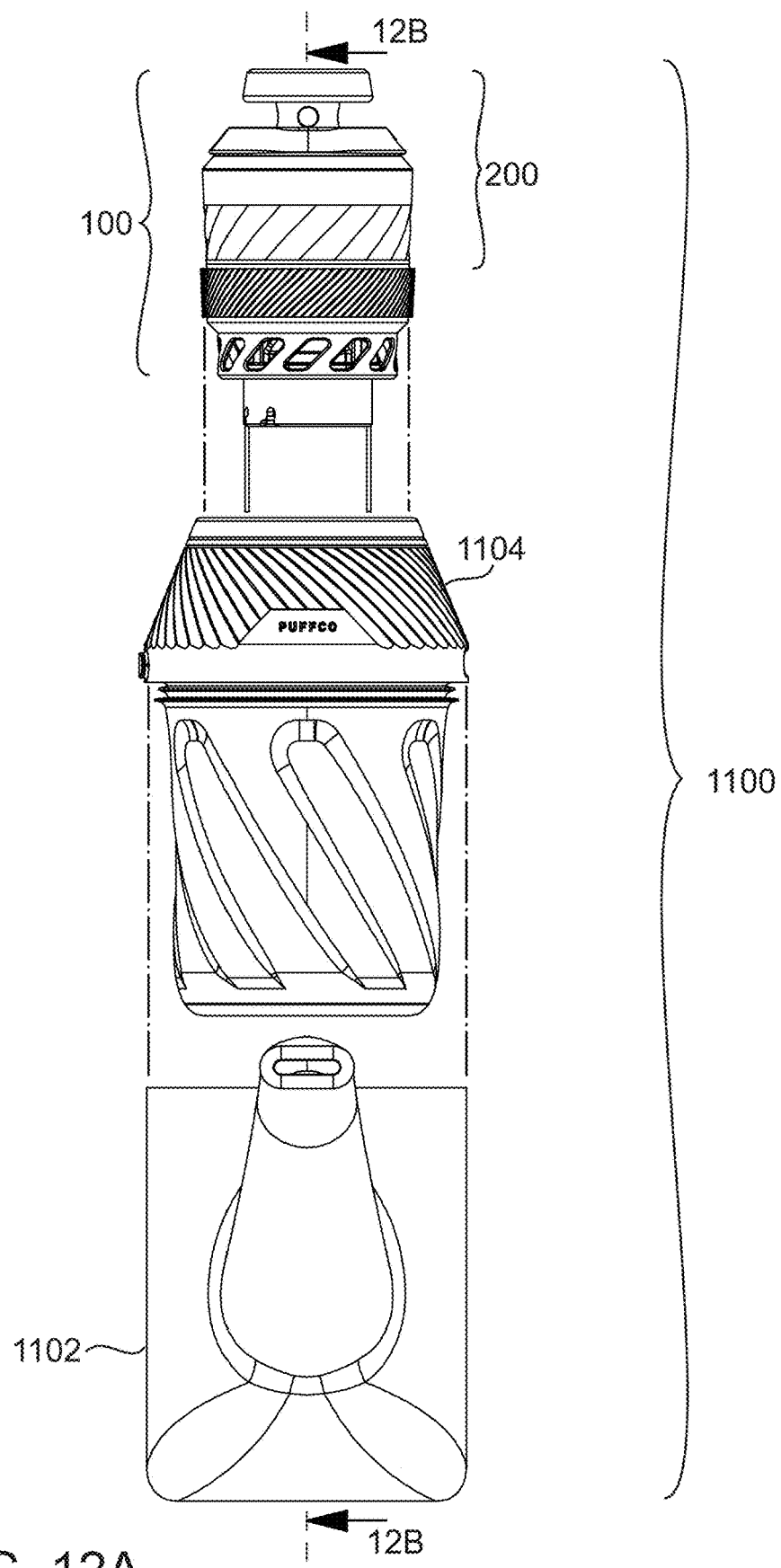
FIG. 12A depicts a front view of an embodiment of the vaporization assembly having a carb cap of FIG. 11 according to aspects of the present disclosure in a closed configuration.

Referring to FIGS. 11 and 12A, an embodiment of another portable electronic vaporizing device 1100 is shown in exploded views according to aspects of the disclosure herein. In some embodiments, the portable electronic vaporization device 1100 comprises a carb cap 200 that is attachable to a removably attachable vaporization assembly 400, a base portion 1104, and a mouthpiece 1102 configured to receive a flow of gas having vaporizable product entrained therein from the removably attachable vaporization assembly 400. In some embodiments, the vaporization assembly 400 is removably attachable to the base portion 1104. In another embodiment, at least a portion of the vaporization assembly 400 connects to the base portion 1104 at an exterior side of the seal formed between the module housing 1120 and the mouthpiece housing 1106.

Figure 12B:
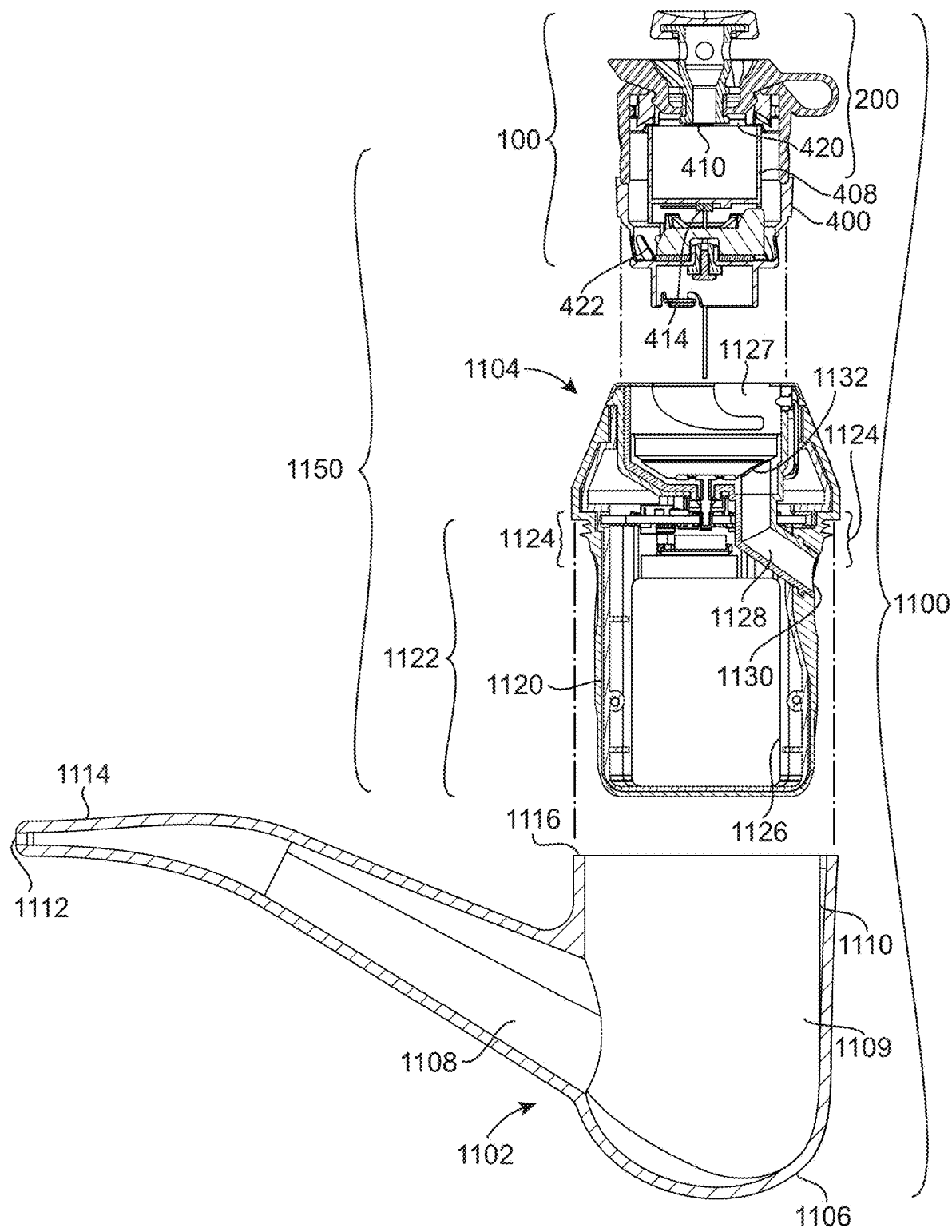
FIG. 12B depicts a cross-section taken along line 12B of FIG. 12A and shows an embodiment of a vaporization assembly having a carb cap according to aspects of the present disclosure.

Referring to FIG. 12B, in some embodiments, the mouthpiece 1102 includes: a mouthpiece housing 1106 at least partly defining an interior chamber 1108; an inhalation outlet 1112 formed in the mouthpiece housing 1106; and a receiving area 1109 for receiving the removably attachable vaporization assembly 1400 in the interior chamber 1108 of the mouthpiece housing 1106.

In some embodiments, the base portion 1104 comprises a module housing 1120 having an insert portion 1122 configured to be at least partly received within the receiving area 1109 of the mouthpiece housing 1106, the insert portion 1122 having one or more sealing regions 1124 configured to form a seal between the module housing 1120 and the mouthpiece housing 1106, and a battery receiving area 1126 disposed within the insert portion 1122 and configured to receive a battery for powering the vaporization assembly 400, and a vaporization assembly receiving area 1127 configured to receiving the vaporization assembly 400.

In some embodiments, the base portion 1104 comprises a gas flow conduit 1128 having an input opening 1132 and an output opening 1130 positioned to output the flow of gas from the removably attachable vaporization assembly 400 to the receiving area 1109 of the mouthpiece 1102 at an interior side of the seal between the module housing 1120 and the mouthpiece housing 1106.

In some embodiments, the vaporization assembly 400 comprises a vaporization assembly housing 440; a vaporizable product container 408 configured to receiving a vaporizable product within the vaporization assembly 400; a heating device 414 configured to be electrically connected to a battery and transfer energy to the vaporizable product in the vaporizable product container 408 to heat the product and form a vapor therefrom; an inlet 410 configured to introduce gas into the vaporizable product container 408; one or more vaporization assembly housing outlets 422 configured to receive a flow of gas having vaporized product entrained therein from the vaporizable product container 408, and where the vaporization assembly housing outlets 422 are configured to provide the flow of gas received form the vaporizable product container 408 to the base portion input opening 1132 of the gas flow conduit 1128 in the base portion 1104.

In some embodiments, in operation of the portable electronic vaporization device 1100, the flow of gas having the vaporized product entrained therein is passed through the gas flow conduit 1128 and received into the receiving area 1109 of the mouthpiece 1102 from the output opening 1130 of the gas flow conduit 1128, and is passed along the interior chamber 1108 of the mouthpiece 1102 to the inhalation outlet 1112. In one embodiment, the gas flow conduit 1128 extends from the input opening 1132 formed in the bottom wall of the vaporization assembly receiving area 1127 to the output opening 1130, and the output opening 1130 of the gas flow conduit 1128 is formed on an outer surface of the insert portion 1122 of the module housing 1120 and is radially external to the input opening 1132.

In some embodiments, the battery receiving area 1126 is configured to be entirely received within the receiving area 1109 of the mouthpiece 1102, such that a battery received in the battery receiving area 1126 is enclosed by the mouthpiece housing 1106. In one embodiment, in operation of the device, the flow of gas having vaporized product entrained therein is flowed past at least a portion of the battery receiving area 1126 of the insert portion 1122 before reaching the inhalation outlet 1112.

In some embodiments, the mouthpiece housing 1106 at least partly defines an interior chamber 1108 having a first end 1114 and a second end 1116, the inhalation outlet 1112 is formed in the mouthpiece housing 1106 in the first end 1114 of the interior chamber 1108, and the receiving area 1109 for receiving the removable battery powered vaporization assembly 400 is at the second end 1116 of the interior chamber 1108 within the mouthpiece housing 1106.

In some embodiments, the at least one of the one or more vaporization assembly outlets 422 is aligned with the input opening 1132 of the gas flow conduit 1128 in the base portion 1104. In one embodiment, the at least one of the one or more vaporization assembly outlets 422 are at a lower region of the vaporization assembly housing 440 that is configured to be engaged to the input opening 1132 of the gas flow conduit 1128, the input opening being formed in the bottom wall of the vaporization assembly receiving area 1127 of the base portion 1104.

In some embodiments, the internal gas flow passage is defined between the vaporization assembly housing 440 and walls of the vaporizable product container 408, radially external to the vaporizable product container 408, and wherein the internal gas flow passage redirects the flow of gas received from one or more vaporizable product container outlets 420 in a direction towards the receiving area 1109 in the mouthpiece 1102.

In some embodiments, the output opening 1130 of the gas flow conduit 1128 is positioned to output the flow of gas from the removably attachable vaporization module 1150 to one or more of: (i) a region of the receiving area 1109 adjacent the module housing 1120, and between the module housing 1120 and the mouthpiece housing 1106; and (ii) a region of the receiving area 1109 below the module housing 1120.

According to another aspect of the present disclosure, a method of using the portable electronic vaporizing device disclosed herein is provided. For example, the method may comprise attaching the carb cap 200 to a vaporization assembly 400 of a vaporization device, and during operation of the vaporization device (e.g., heating the vaporizable product within the container 408 of the vaporization assembly 400 with the heating device 414), moving the movable gas introduction stem 202 to direct a flow of gas entering the vaporization assembly 400.

Embodiments

The Enumerated Embodiments 1-100 below set forth embodiments according to the disclosure.

Embodiment 1. A carb cap for a vaporization assembly, the carb cap comprising:
- a vaporization assembly attachment configured to be attached to the vaporization assembly,
- a movable gas introduction stem configured to introduce gas into the vaporization assembly, the movable gas introduction stem comprising:
  one or more gas inlets located towards a first end of the movable gas introduction stem configured to receive a flow of gas, a gas outlet located towards a second end of the movable gas introduction stem configured to introduce the flow of gas into the vaporization assembly, and a gas flow conduit through the movable gas introduction stem connecting the one or more gas inlets to the gas outlet, and
- a flexible diaphragm extending between the movable gas introduction stem and the vaporization assembly attachment.

Embodiment 2. The carb cap for the vaporization assembly according to Embodiment 1, wherein the flexible diaphragm is configured to flex in relation to a force applied by a user to the movable gas introduction stem, to allow the movable gas introduction stem to move independently of the vaporization assembly attachment in response to the applied force.

Embodiment 3. The carb cap for a vaporization assembly according to any preceding Embodiment, wherein the vaporization assembly attachment is configured to be attached to one or more structures of the vaporization assembly, including any one or more of an upper wall of the vaporization assembly, a portion of a vaporization assembly housing, a container configured to hold vaporizable product within the vaporization assembly, an annular insert disposed over the container, and/or a heating device of a vaporization assembly.

Embodiment 4. The carb cap for a vaporization assembly according to any preceding Embodiment, wherein the vaporization assembly attachment is configured to be attached to an annular insert disposed over the container that is configured to hold vaporizable product within the vaporization assembly.

Embodiment 5. The carb cap for a vaporization assembly according to any preceding Embodiment, wherein vaporization assembly attachment is configured to be attached to an annular insert disposed over the container that is configured to hold vaporizable product within the vaporization assembly, and wherein at least a portion of the vaporization assembly attachment is configured to extend over the top and outer surface of the vaporization assembly housing.

Embodiment 6. The carp cap for a vaporization assembly according to Embodiment 5, wherein the vaporization assembly attachment comprises an upper attachment segment that is configured to engage the annular insert, and a lower attachment segment that is configured to be mounted to an upper portion of the vaporization assembly housing.

Embodiment 7. The carb cap for a vaporization assembly according to Embodiment 6, wherein the upper attachment segment is removably attachable from the lower attachment segment to allow for access to an interior of the vaporization assembly while the lower attachment segment remains mounted on the vaporization assembly housing, and optionally wherein the upper and lower attachment segments are connected via a tether.

Embodiment 8. The carb cap for a vaporization assembly according to any of Embodiments 6-7, wherein the upper attachment segment comprises one or more annular sealing ribs that are configured to engage a complementary channel on an inner wall of the annular insert, and wherein the lower attachment segment comprises an annular jacket that surrounds a periphery of the upper portion of the vaporization assembly housing.

Embodiment 9. The carb cap for a vaporization assembly according to any preceding Embodiment, wherein the vaporization assembly attachment is configured to form an airtight seal with the vaporization assembly when attached thereto.

Embodiment 10. The carb cap for a vaporization assembly according to any preceding Embodiment, wherein the movable gas introduction stem is rotatable with respect to a central axis passing through the carb cap in a first direction, in response to a force applied by the user to the movable gas introduction stem.

Embodiment 11. The carb cap for a vaporization assembly according to any preceding Embodiment, wherein the movable gas introduction stem is rotatable away from the central axis by at least 5, at least 10, at least 15, at least 20, at least 30, and/or at least 45 degrees.

Embodiment 12. The carp cap for a vaporization assembly according to any preceding Embodiment, wherein the movable gas introduction stem is configured to be deflected away from a central axis passing through the carb cap in a first direction, in response to a force applied by the user to the movable gas introduction stem.

Embodiment 13. The carb cap for a vaporization assembly according to any preceding Embodiment, wherein the movable gas introduction stem is deflected away from the central axis by at least 5, at least 10, at least 15, at least 20, at least 30, and/or at least 45 degrees.

Embodiment 14. The carb cap for a vaporization assembly according to any preceding Embodiment, wherein the movable gas introduction stem is capable of being tilted radially away from a central axis passing through the carb cap in a first direction.

Embodiment 15. The carb cap for a vaporization assembly according to any preceding Embodiment, wherein the movable gas introduction stem is capable of being tilted away from the central axis by at least 5, at least 10, at least 15, at least 20, at least 30, and/or at least 45 degrees.

Embodiment 16. The carb cap for a vaporization assembly according to any preceding Embodiment, wherein the central axis passes through a center of the carb cap in the vertical direction.

Embodiment 17. The carb cap for a vaporization assembly according to any preceding Embodiment, wherein the vaporization assembly attachment has an outer edge and an inner edge, wherein the inner edge is radially interior to the outer edge, and a degree to which the movable gas introduction stem can be tilted radially away from the central axis is limited by contact with the vaporization assembly attachment inner edge.

Embodiment 18. The carb cap for a vaporization assembly according to any preceding Embodiment, wherein the flexible diaphragm and the vaporization assembly attachment are one piece.

Embodiment 19. The carb cap for a vaporization assembly according to any preceding Embodiment, wherein the flexible diaphragm and the vaporization assembly are separate pieces configured to be removably attached to each other.

Embodiment 20. The carb cap for a vaporization assembly according to any preceding Embodiment, wherein the movable gas introduction stem is a separate piece from the flexible diaphragm.

Embodiment 21. The carb cap for a vaporization assembly according to any preceding Embodiment, wherein the flexible diaphragm and the movable gas introduction stem are one piece.

Embodiment 22. The carb cap for a vaporization assembly according to any preceding Embodiment, wherein the movable gas introduction stem is removably attachable to the flexible diaphragm.

Embodiment 23. The carb cap for a vaporization assembly according to any preceding Embodiment, wherein the vaporization assembly attachment, the flexible diaphragm, and the movable gas introduction stem are one piece.

Embodiment 24. The carb cap for a vaporization assembly according to any preceding Embodiment, wherein the movable gas introduction stem comprises a cover configured to at least partly cover the first end of the movable gas introduction stem.

Embodiment 25. The carb cap for a vaporization assembly according to any preceding Embodiment, wherein the movable gas introduction stem cover comprises an elastomeric material.

Embodiment 26. The carb cap for a vaporization assembly according to any preceding Embodiment, wherein the movable gas introduction stem cover comprises silicone.

Embodiment 27. The carb cap for a vaporization assembly according to any preceding Embodiment, wherein the flexible diaphragm is an elastomeric material.

Embodiment 28. The carb cap for a vaporization assembly according to any preceding Embodiment, wherein the flexible diaphragm comprises silicone.

Embodiment 29. The carb cap for a vaporization assembly according to any preceding Embodiment, wherein the movable gas introduction stem and the movable gas introduction stem cover are one piece.

Embodiment 30. The carb cap for a vaporization assembly according to any preceding Embodiment, wherein the movable gas introduction stem has a central stem aperture open at the first end and one or more gas inlets between the first end and the second end, and wherein the movable gas introduction stem cover is configured to seal closed the central stem aperture.

Embodiment 31. The carb cap for a vaporization assembly according to any preceding Embodiment, wherein the cover of the movable gas introduction stem comprises a handle for control of the movable gas introduction stem by the user.

Embodiment 32. The carb cap for a vaporization assembly according to any preceding Embodiment, wherein the one or more gas inlets comprise a plurality of gas inlets located towards the first end of the movable gas introduction stem, the plurality of gas inlets being circumferentially disposed about the gas flow conduit within the movable gas introduction stem.

Embodiment 33. The carb cap for a vaporization assembly according to any preceding Embodiment, wherein the movable gas introduction stem comprises an elongate housing (217, see FIG. 3) for the gas flow conduit, and wherein the plurality of gas inlets pass through the elongate housing at a plurality of circumferentially disposed positions about the gas flow conduit.

Embodiment 34. The carb cap for a vaporization assembly according to any preceding Embodiment, wherein the vaporization assembly comprises: a vaporization assembly housing configured to house a container that is configured to hold a vaporizable product, and a heating device configured to heat vaporizable product held in the container, and optionally wherein the heating device is battery powered.

Embodiment 35. The carb cap for a vaporization assembly according to Embodiment 34, wherein the vaporization assembly comprises a vaporization assembly inlet configured to introduce gas into the vaporization assembly, and a vaporization assembly outlet configured to exhaust gas from the vaporization assembly.

Embodiment 36. The carb cap for a vaporization assembly according to any preceding Embodiment, wherein the vaporization assembly housing comprises one or more vaporization assembly housing walls that at least partially define a vaporization assembly internal flow path leading from the container to the vaporization assembly outlet.

Embodiment 37. The carb cap for a vaporization assembly according to Embodiment 36, wherein the vaporization assembly attachment section attaches to an annular insert disposed over a container held in the vaporization assembly housing, and wherein the annular insert comprises a plurality of channels disposed about a circumference thereof that form container outlets with a top surface of a sidewall of the container, and wherein the vaporization assembly internal flow path forms a path leading from the container outlets to the vaporization assembly outlet.

Embodiment 38. The carb cap for a vaporization assembly according to any preceding Embodiment, wherein the movable gas introduction stem comprises a central stem aperture for the gas flow conduit, and wherein the plurality of gas inlets pass through the central stem aperture at a plurality of circumferentially disposed positions about the central stem aperture for the gas flow conduit.

Embodiment 39. The carb cap for a vaporization assembly according to any preceding Embodiment, wherein the vaporization assembly comprises a vaporization assembly housing and a vaporization assembly inlet at a top end of the vaporization assembly, and wherein the carb cap is configured to be attached to the vaporization assembly such that the carb cap is positioned over the vaporization assembly inlet.

Embodiment 40 The carb cap for a vaporization assembly according to any preceding Embodiment, wherein the vaporization assembly is further configured to contain a vaporizable product container within a vaporization assembly housing, wherein the vaporizable product container is configured to hold vaporizable product therein.

Embodiment 41. The carb cap for a vaporization assembly according to any preceding Embodiment, wherein the vaporization assembly further comprises a heating element comprising one or more resistive heating traces capable of heating the vaporizable product.

Embodiment 42. The carb cap for a vaporization assembly according to any preceding Embodiment, wherein when the vaporization assembly attachment comprising the flexible diaphragm is attached to the vaporization assembly, the flexible diaphragm is configured to extend radially inwardly over a vaporization assembly inlet at the top end of the vaporization assembly.

Embodiment 43. The carb cap for a vaporization assembly according to any preceding Embodiment, wherein the degree of movement of the movable gas introduction stem is proportional to the extent of movement of the flexible diaphragm in response the force applied by the user.

Embodiment 44. The carb cap for a vaporization assembly according to any preceding Embodiment, wherein the movable gas introduction stem has an elongate housing comprising a radially exterior wall, and wherein the radially exterior wall comprises a sealing region formed about a circumference of the exterior wall.

Embodiment 45. The carb cap for a vaporization assembly according to any preceding Embodiment, wherein the sealing region extends entirely about a circumference of the exterior wall.

Embodiment 46. The carb cap for a vaporization assembly according to any preceding Embodiment, wherein the flexible diaphragm has a flexible arm at a radially interior end of the flexible diaphragm, wherein the flexible arm comprises one or more sealing surfaces configured to provide an airtight seal with the movable gas introduction stem along the sealing region on the radially exterior wall when the movable gas introduction stem is attached to the flexible diaphragm.

Embodiment 47. The carb cap for a vaporization assembly according to any preceding Embodiment, wherein the sealing region on the radially exterior wall comprises upper and lower sealing region ridges that engage and retain the flexible arm of the flexible diaphragm therebetween.

Embodiment 48. The carb cap for a vaporization assembly according to any preceding Embodiment, wherein the removably attachable movable gas introduction stem is configured to be removed from attachment with the flexible diaphragm by pulling outwardly with a force that exceeds a retaining force of the sealing region on the radially exterior wall of the movable gas introduction stem when the movable gas introduction stem is attached to the flexible diaphragm.

Embodiment 49. The carb cap for a vaporization assembly according to any preceding Embodiment, wherein a detached removably attachable movable gas introduction stem is configured to be re-attached to the flexible diaphragm by pushing inwardly with a force that exceeds a resistive force of the sealing region on the radially exterior wall of the movable gas introduction stem when the movable gas introduction stem is pushed into attachment with the flexible diaphragm, and wherein the removably attachable movable gas introduction stem is attached to the flexible diaphragm when the one or more sealing surfaces of the flexible arm of the flexible diaphragm forms an airtight seal with the movable gas introduction stem sealing region.

Embodiment 50. The carb cap for a vaporization assembly according to any preceding Embodiment, wherein movement of the movable gas introduction stem with respect to the flexible diaphragm flexible arm does not break an airtight seal between the flexible diaphragm and the movable gas introduction stem.

Embodiment 51. The carb cap for a vaporization assembly according to any preceding Embodiment, wherein movement of the movable gas introduction stem results in substantially no translation between the sealing surfaces of the flexible arm of the flexible diaphragm and the sealing region of the movable gas introduction stem.

Embodiment 52. The carb cap for a vaporization assembly according to any preceding Embodiment, wherein the flexible diaphragm comprises a flexible arm that forms a flexible joint with a main body of the flexible diaphragm.

Embodiment 53. The carb cap for a vaporization assembly according to any preceding Embodiment, wherein when the one or more sealing surfaces of the flexible arm of the flexible diaphragm are substantially parallel with the movable gas introduction stem sealing region, and wherein the one or more sealing surfaces are substantially perpendicular to the main body of the flexible diaphragm when the movable gas introduction stem is aligned parallel to a central axis.

Embodiment 54. The carb cap for a vaporization assembly according to any preceding Embodiment, wherein the movable gas introduction stem sealing region is configured to retain the movable gas introduction stem as received by the flexible diaphragm when the movable gas introduction stem is attached to the flexible diaphragm.

Embodiment 55. The carb cap for a vaporization assembly according to any preceding Embodiment, wherein the flexible diaphragm comprises a central aperture for receiving the movable gas introduction stem, the flexible diaphragm comprising a flexible arm at the radially interior end of the flexible diaphragm and about a perimeter of the central aperture that engages the sealing region of the removable gas introduction stem.

Embodiment 56. The carb cap for a vaporization assembly according to any preceding Embodiment, wherein a vertical cross-section of the flexible diaphragm is thinner than the vertical cross-section of the vaporization assembly attachment.

Embodiment 57. The carb cap for a vaporization assembly according to any preceding Embodiment, wherein the vertical cross-section thickness of the flexible diaphragm is tapered radially inward so that the radially interior end is thinner than a radially exterior end of the flexible diaphragm.

Embodiment 58. The carb cap for a vaporization assembly according to any preceding Embodiment, wherein the flexible diaphragm is biased to return the movable gas introduction stem to a resting position aligned with the central axis when no force is being applied by the user.

Embodiment 59. The carb cap for a vaporization assembly according to any preceding Embodiment, wherein the gas flow conduit is a Venturi-type shape.

Embodiment 60. The carb cap for a vaporization assembly according to any preceding Embodiment, wherein the gas flow conduit is wider toward the first end of the movable gas introduction stem than at the second end of the movable gas introduction stem.

Embodiment 61. The carb cap for a vaporization assembly according to any preceding Embodiment, wherein the gas flow conduit has a first volume adjacent to the one or more gas inlets at the first end of the movable gas introduction stem and a second volume adjacent the gas outlet and located towards the second end of the movable gas introduction stem, wherein the first volume is larger than the second volume.

Embodiment 62. The carb cap for a vaporization assembly according to any preceding Embodiment, wherein the velocity of gas flowing through the gas flow conduit increases from the first end to the second end of the movable gas introduction stem when the movable gas introduction stem is attached to the vaporization assembly attachment and the vaporization device is in operation.

Embodiment 63. The carb cap for a vaporization assembly according to any preceding Embodiment, wherein the vaporization assembly attachment comprises a jacket that is configured to attach to walls of a vaporization assembly housing.

Embodiment 64. The carb cab for a vaporization assembly according to any preceding Embodiment, wherein the vaporization assembly attachment comprises a lower segment comprising the jacket that is configured to mount to the walls of the vaporization assembly by extending over an outer surface of the sidewall of the vaporization assembly housing, the jacket forming a hollow tube extending over the outer surface, and the jacket having an upper annular rim configured to be disposed at an upper end of the vaporization assembly and that engages a lower sealing surface of the upper segment of the vaporization assembly attachment, to form a seal with the upper segment when the upper segment is in a closed position over the vaporization assembly.

Embodiment 65. The carb cap for a vaporization assembly according to any preceding Embodiment, wherein the vaporization assembly attachment comprises sealing surfaces about a periphery thereof that seal to structures of the vaporization assembly.

Embodiment 66. The carb cap for a vaporization assembly according to any preceding Embodiment, wherein the vaporization assembly attachment is removably attachable to the vaporization assembly.

Embodiment 67. The carb cap for a vaporization assembly according to any preceding Embodiment, wherein the movable gas introduction stem cover comprises a concave depression to fit a tip of a finger of the user.

Embodiment 68. The carb cap for a vaporization assembly according to any preceding Embodiment, wherein the movable gas introduction stem cover comprises a rounded convex protrusion to fit a tip of a finger of the user.

Embodiment 69. The carb cap for a vaporization assembly according to any preceding Embodiment, wherein the vaporization assembly attachment comprises an upper segment and a lower segment, wherein the upper segment is attached to the movable gas introduction stem through the flexible diaphragm, and the lower segment is configured to attach to a vaporization assembly housing.

Embodiment 70. The carb cap for a vaporization assembly according to any preceding Embodiment, wherein the vaporization assembly attachment upper segment and the vaporization assembly attachment lower segment are two separate pieces and can be detached from each other in an open configuration of the vaporization assembly attachment, to provide access to an interior of the vaporization assembly.

Embodiment 71. The carb cap for a vaporization assembly according to any preceding Embodiment, wherein a tether connects the vaporization assembly attachment upper segment and lower segment.

Embodiment 72. The carb cap for a vaporization assembly according to any preceding Embodiment, wherein the tether between the upper and lower segments maintains a connection between the upper and lower segments when the vaporization assembly attachment is in the open configuration.

Embodiment 73. The carb cap for a vaporization assembly according to any preceding Embodiment, wherein the carb cap is configured to be attached to a vaporization assembly comprising a vaporization assembly housing with an vaporization assembly inlet, and a vaporizable product container for holding vaporizable product within the vaporization assembly housing, and wherein during operation of the vaporization assembly, a direction of gas flowing out of the gas outlet of the movable gas introduction stem into the container in the vaporization assembly housing is controlled by the movement of the movable gas introduction stem in response to the force applied by the user.

Embodiment 74. A vaporization assembly comprising the carb cap according to any preceding Embodiment, wherein the vaporization assembly comprises a vaporization assembly housing, a vaporizable product container for holding vaporizable product within the vaporization assembly housing, and a heating device configured to heat vaporizable product held in the vaporizable product container.

Embodiment 75. A vaporization assembly comprising the carb cap according to any preceding Embodiment, wherein the vaporization assembly comprises a vaporization assembly inlet configured to introduce gas into the vaporization assembly, and a vaporization assembly outlet configured to exhaust gas from the vaporization assembly.

Embodiment 76. A vaporization assembly comprising the carb cap according to any preceding Embodiment, wherein the vaporization assembly comprises a vaporization assembly housing having one or more vaporization assembly housing walls that at least partially define a vaporization assembly internal flow path leading from the container to the vaporization assembly outlet.

Embodiment 77. A vaporization assembly comprising the carb cap according to Embodiment 76, wherein the vaporization assembly attachment section attaches to an annular insert disposed over a container held in a vaporization assembly housing, and wherein the annular insert comprises a plurality of channels disposed about a circumference thereof that form container outlets with a top surface of a sidewall of the container, and wherein the vaporization assembly internal flow path forms a path leading from the container outlets to the vaporization assembly outlet.

Embodiment 78. A portable electronic vaporization device comprising the carb cap according to any preceding Embodiment.

Embodiment 79. A portable electronic vaporization device according to Embodiment 78, wherein the device comprises a vaporization assembly according to any of Embodiments 74-77, a carp cap according to any preceding Embodiment, and a mouthpiece configured to receive vaporizable product that is vaporized in the container, the mouthpiece having an inhalation outlet for inhaling of the vaporized product.

Embodiment 80. The portable electronic vaporization device according to Embodiment 79, wherein the container used to hold vaporizable product comprises: container walls comprising one or more sidewalls and a bottom wall that form a space to receive the vaporizable product, and a heating device comprising one or more resistive heating traces embedded in one or more of the container walls, the heating device configured to be electrically connected to a battery and transfer energy to the vaporizable product in the container to heat the product and form a vapor therefrom.

Embodiment 81. The portable electronic vaporizing device according to any preceding Embodiment, wherein portable electronic vaporizing device comprises: a base having a gas flow path conduit therein and a housing for one or more components for powering and/or controlling the device, the gas flow path conduit comprising a conduit inlet and a conduit outlet;
  a mouthpiece that is removably attachable to the base, the mouthpiece comprising:
    a mouthpiece housing comprising one or more mouthpiece walls at least partly defining a mouthpiece internal flow path through the mouthpiece housing;
    an inhalation outlet formed in a region of the one or more mouthpiece walls; and
    at least one mouthpiece inlet capable of being placed in communication with the conduit outlet of the base upon attachment of the mouthpiece to the base, to receive a flow of gas into the mouthpiece from the base; and
  a vaporization assembly that is removably attachable to the base, the vaporization assembly comprising:
    a carb cap according to any preceding Embodiment;
    a vaporization assembly inlet configured to receive a flow of gas into the vaporization assembly;
    a vaporization assembly housing comprising one or more vaporization assembly housing walls that at least partially define an vaporization assembly internal flow path therein;
    a container within the vaporization assembly housing that is capable of holding a vaporizable product,
    a heating device capable of heating the vaporizable product held in the container, the heating device being configured to be electrically connected to the one or more components for powering and/or controlling the device that are housed in the base;
    a container inlet capable of introducing gas into the container to entrain vaporizable product;
    one or more container outlets capable of flowing the gas having the vaporizable product entrained therein into vaporization assembly internal flow path; and
    one or more vaporization assembly outlets capable of receiving the flow of gas from the vaporization assembly internal flow path, and providing the flow of gas to the conduit inlet of the base,
    wherein at least a portion of the vaporization assembly internal flow path in the vaporization assembly is defined between the one or more vaporization assembly housing walls and one or more sidewalls of the container, and
    wherein the flow of gas having the vaporizable product entrained therein flows from the vaporization assembly internal flow path and through the gas flow conduit inlet of the base to the mouthpiece inlet, and along the mouthpiece internal flow path to the inhalation outlet.

Embodiment 82. The portable electronic vaporizing device according to any preceding Embodiment, wherein the vaporization assembly is removable from the base independently of removal of the mouthpiece.

Embodiment 83. The portable electronic vaporizing device according to any preceding Embodiment, wherein the vaporization assembly comprises a heating device disposed below a bottom surface of the container that adapted to receive the vaporizable product.

Embodiment 84. The portable electronic vaporizing device according to any preceding Embodiment, wherein the vaporization assembly comprises a heating device comprising one or more heating traces embedded in a wall of the container.

Embodiment 85. The portable electronic vaporizer device according to any preceding Embodiment, wherein the one or more second container outlets in the vaporization assembly that flow the gas having the vaporizable product entrained therein out of the container and into the vaporization assembly internal flow path, are located towards a top end of the vaporization assembly and radially externally to the first container inlet, and are positioned in an arrangement circumferentially surrounding the first container inlet.

Embodiment 86. The portable electronic vaporizing device according to any preceding Embodiment, wherein the one or more second container outlets comprise: one or more apertures formed between a top surface of the container and an annular insert disposed above the container, the annular ring comprising one or more indentations formed in a bottom surface about a circumference thereof that form the one or more apertures between the bottom surface of the annular ring and the top surface of the container.

Embodiment 87. The portable electronic vaporizer device according to any preceding Embodiment, wherein the flow of gas through the vaporization assembly comprises flow through a container inlet into a top of the container, flow out of the container through container outlets that are separate from the inlet and disposed towards a top end of the vaporization assembly, and wherein the vaporization assembly housing at least partially directs gas from the one or more second container gas outlets along the internal vaporization assembly gas flow path, in a passage formed between walls of the container and the vaporization assembly housing, and wherein the vaporization assembly housing comprises one or more outlets formed therein to flow gas from the internal vaporization assembly gas flow path to a conduit in the base portion.

Embodiment 88. The portable electronic vaporizer device according to any preceding Embodiment, wherein the mouthpiece internal flow path comprises a convoluted flow path from the at least one mouthpiece inlet to the inhalation outlet, the mouthpiece comprising a first chamber that is internal to a second chamber that at least partially circumferentially surrounds the first chamber, and wherein the flow of gas along the mouthpiece internal flow path is received in the at least one mouthpiece inlet, passes through the first chamber and into the second chamber, and out of the inhalation outlet.

Embodiment 89. A portable electronic vaporizing device comprising a removably attachable vaporization module, and a mouthpiece configured to receive a flow of gas having vaporized product entrained therein from the removably attachable vaporization module, wherein the mouthpiece comprises:
a mouthpiece housing at least partly defining an interior chamber;
an inhalation outlet formed in the mouthpiece housing; and
a receiving area for receiving the removable battery powered vaporization module in the interior chamber of the mouthpiece housing, and the removably attachable vaporization module comprises:
a base portion comprising:
a module housing having an insert portion configured to be at least partly received within the receiving area of the mouthpiece housing, the insert portion having one or more sealing regions configured to form a seal between the module housing and the mouthpiece housing, and a battery receiving area disposed within the insert portion and configured to receive a battery for powering the vaporization module; and
a gas flow conduit having an input opening and an output opening positioned to output the flow of gas from the removably attachable vaporization module to the receiving area of the mouthpiece at an interior side of the seal between the module housing and the mouthpiece housing, and
a vaporization assembly comprising;
a carb cap according to any preceding Embodiment;
a vaporization assembly housing;
a container configured to receive a vaporizable product within the vaporization assembly housing;
a heating device configured to be electrically connected to the battery and transfer energy to the vaporizable product in the container to heat the product and form a vapor therefrom;
an inlet configured to introduce gas into the container;
one or more container outlets configured to receive a flow of gas having vaporized product entrained therein from the container; and
one or more vaporization assembly outlets configured to provide the flow of gas received from the container outlets to the input opening of the gas flow conduit in the base portion,
wherein in operation of the portable electronic vaporizing device, the flow of gas having the vaporized product entrained therein is passed through the gas flow conduit and received into the receiving area of the mouthpiece from the output opening of the gas flow conduit, and is passed along the interior chamber of the mouthpiece to the inhalation outlet.

Embodiment 90. The portable electronic vaporizing device according to any preceding Embodiment, wherein the battery receiving area is configured to be entirely received within the receiving area of the mouthpiece, such that a battery received in the battery receiving area is enclosed by the walls of the mouthpiece.

Embodiment 91. The portable electronic vaporizing device according to any preceding Embodiment, wherein the mouthpiece housing at least partly defines an internal channel having a first end and a second end, the inhalation outlet is formed in the mouthpiece housing in the first end of the interior chamber, and the receiving area for receiving the removable battery powered vaporization module is at the second end of the interior chamber within the mouthpiece housing.

Embodiment 92. The portable electronic vaporizing device according to any preceding Embodiment, wherein at least a portion of the vaporization assembly connects to the base portion at an exterior side of the seal formed between the module housing and the mouthpiece housing.

Embodiment 93. The portable electronic vaporizing device according to any preceding Embodiment, wherein the vaporization assembly is removably attachable to the base portion.

Embodiment 94. The portable electronic vaporizing device according to any preceding Embodiment, wherein the one or more vaporization assembly outlets are at a lower region of the assembly housing that is configured to be engaged to the input opening of the gas flow conduit, the input opening being formed in the bottom wall of the vaporization assembly receiving area of the base portion.

Embodiment 95. The portable electronic vaporizing device according to any preceding Embodiment, wherein the gas flow conduit extends from the input opening formed in the bottom wall of the vaporization assembly receiving area to the output opening, and wherein the output opening of the gas flow conduit is formed on an outer surface of the insert portion of the module housing and is radially external to the input opening.

Embodiment 96. The portable electronic vaporizing device according to any preceding Embodiment, wherein at least a portion of the battery receiving area of the removably attachable vaporization module is configured to be received in the receiving area at an interior side of the seal formed between the module housing and the mouthpiece housing.

Embodiment 97. The portable electronic vaporizing device according to any preceding Embodiment, wherein in operation of the device, the flow of gas having vaporized product entrained therein is flowed past at least a portion of the battery receiving area of the insert portion before reaching the inhalation outlet.

Embodiment 98. The portable electronic vaporizing device according to any preceding Embodiment, wherein the output opening of the gas flow conduit is positioned to output the flow of gas from the removably attachable vaporization module to one or more of: (i) a region of the receiving area adjacent the module housing, and between the module housing and the mouthpiece housing; and (ii) a region of the receiving area below the module housing.

Embodiment 99. A vaporization assembly for a portable electronic vaporizing device comprising the carb cap of any preceding Embodiment, the vaporization assembly comprising:
a vaporization assembly housing;
a container configured to receive a vaporizable product within the vaporization assembly housing, the container including a heating device configured to be electrically connected to a power source and transfer energy to the vaporizable product in the container to heat the product and form a vapor therefrom;
an inlet configured to introduce gas into the container;
one or more container outlets configured to receive a flow of gas having vaporized product entrained therein from the container; and
one or more vaporization assembly outlets configured to output the flow of gas received from the container outlets, wherein during use of the vaporization assembly in the portable electronic vaporizing device, the flow of gas output by the one or more vaporization assembly outlets is received by a mouthpiece of the electronic vaporizing device.

Embodiment 100. A method of introducing gas flow into a vaporization assembly, the method comprising:

attaching the carb cap of any of the preceding claims to a vaporization assembly of a vaporization device, and during operation of the vaporization device, moving the movable gas introduction stem to direct a flow of gas entering a vaporization assembly housing.

EQUIVALENTS

While specific embodiments have been discussed, the above specification is illustrative, and not restrictive. Many variations will become apparent to those skilled in the art upon review of this specification. The full scope of the embodiments should be determined by reference to the claims, along with their full scope of equivalents, and the specification, along with such variations.

What is claimed is:

1. A carb cap for a vaporization assembly, the carb cap comprising:
   a vaporization assembly attachment configured to be attached to the vaporization assembly,
   a movable gas introduction stem configured to introduce gas into the vaporization assembly, the movable gas introduction stem comprising:
      one or more gas inlets located towards a first end of the movable gas introduction stem configured to receive a flow of gas, a gas outlet located towards a second end of the movable gas introduction stem configured to introduce the flow of gas into the vaporization assembly, and a gas flow conduit through the movable gas introduction stem connecting the one or more gas inlets to the gas outlet, and
   a flexible diaphragm extending between the movable gas introduction stem and the vaporization assembly attachment,
   wherein the flexible diaphragm is configured to flex in relation to a force applied by a user to the movable gas introduction stem, to allow the movable gas introduction stem to move independently of the vaporization assembly attachment in response to the applied force.

2. The carb cap according to claim 1, wherein the vaporization assembly attachment is configured to be attached to one or more structures of the vaporization assembly, including any one or more of an upper wall of the vaporization assembly, a portion of a vaporization assembly housing, a container configured to hold vaporizable product within the vaporization assembly, an annular insert disposed over the container, and/or a heating device of the vaporization assembly.

3. The carb cap according to claim 2, wherein the vaporization assembly attachment is configured to be attached to the annular insert disposed over the container.

4. The carb cap according to claim 1, wherein the movable gas introduction stem is rotatable with respect to a central axis passing through the carb cap in a vertical direction, in response to the force applied by the user to the movable gas introduction stem.

5. The carb cap according to claim 4, wherein the vaporization assembly attachment has an outer edge and an inner edge, wherein the inner edge is radially interior to the outer edge, and a degree to which the movable gas introduction stem can be rotated radially away from the central axis is limited by contact with the vaporization assembly attachment inner edge.

6. The carb cap according to claim 4, wherein the flexible diaphragm is biased to return the movable gas introduction stem to a resting position aligned with the central axis of the carb cap when no force is being applied by the user.

7. The carb cap according to claim 1, wherein when the vaporization assembly attachment comprising the flexible diaphragm is attached to the vaporization assembly, the flexible diaphragm is configured to extend radially inwardly over a vaporization assembly inlet at a top end of the vaporization assembly.

8. The carb cap according to claim 1, wherein a degree of movement of the movable gas introduction stem is proportional to an extent of movement of the flexible diaphragm in response the force applied by the user.

9. The carb cap according to claim 1, wherein the movable gas introduction stem has an elongate housing comprising a radially exterior wall, and wherein the radially exterior wall comprises a sealing region formed about a circumference of the radially exterior wall.

10. The carb cap according to claim 9, wherein the flexible diaphragm has a flexible arm at a radially interior end of the flexible diaphragm, and wherein the flexible arm comprises one or more sealing surfaces configured to provide an airtight seal with the movable gas introduction stem along the sealing region of the radially exterior wall.

11. The carb cap according to claim 10, wherein movement of the movable gas introduction stem results in substantially no translation between the sealing surfaces of the flexible arm of the flexible diaphragm and the sealing region of the radially exterior wall.

12. The carb cap according to claim 1, wherein the movable gas introduction stem has a central stem aperture open at the first end of the movable gas introduction stem and the one or more gas inlets between the first end and the second end of the movable gas introduction stem, and wherein a movable gas introduction stem cover is configured to seal closed the central stem aperture.

13. The carb cap according to claim 12, wherein the one or more gas inlets between the first end and the second end of the movable gas introduction stem pass through the central stem aperture at a plurality of circumferentially disposed positions about the central stem aperture for the gas flow conduit.

14. The carb cap according to claim 12, wherein the movable gas introduction stem cover comprises a handle for control of the movable gas introduction stem by the user.

15. The carb cap according to claim 12, wherein movable gas introduction stem cover comprises a concave depression to fit a tip of a finger of the user.

16. The carb cap according to claim 12, wherein the movable gas introduction stem and the movable gas introduction stem cover are one piece.

17. The carb cap according to claim 1, wherein the flexible diaphragm forms an airtight connection with the movable gas introduction stem.

18. The carb cap according to claim 1, wherein the gas flow conduit of the movable gas introduction stem is a Venturi-type shape that is wider toward the first end of the movable gas introduction stem than at the second end of the movable gas introduction stem.

19. The carb cap according to claim 1, wherein the gas flow conduit has a first volume adjacent to the one or more gas inlets at the first end of the movable gas introduction stem and a second volume adjacent to the gas outlet and located towards the second end of the movable gas introduction stem, wherein the first volume is larger than the second volume.

20. The carb cap according to claim 1, wherein the velocity of air flowing through the gas flow conduit increases from the first end to the second end of the movable gas introduction stem.

21. The carb cap according to claim 1, wherein the vaporization assembly attachment comprises an upper attachment segment that is removably attachable to a lower attachment segment, wherein the upper attachment segment is connected to the flexible diaphragm and the lower attachment segment is configured to be attached to a vaporization assembly housing, and wherein the upper and lower attachment segments are optionally connected together by a tether.

22. The carb cap according to claim 21, wherein the lower attachment segment comprises a jacket that is capable of being mounted over top ends of walls of the vaporization assembly housing.

23. The carb cap according to claim 22, wherein the jacket is configured to mount to the walls of the vaporization assembly housing by extending over an outer surface of the sidewall of the vaporization assembly housing, the jacket forming a hollow tube extending over the outer surface, and the jacket having an upper annular rim configured to be disposed at an upper end of the vaporization assembly housing and that engages a lower sealing surface of the upper attachment segment of the vaporization assembly attachment, to form a seal with the upper attachment segment when the upper attachment segment is in a closed position over the vaporization assembly.

24. The carb cap according to claim 1, wherein the flexible diaphragm is made of an elastomeric material.

25. The carb cap according to claim 24, wherein the flexible diaphragm comprises silicone.

26. The carb cap according to claim 1, wherein a direction of gas flowing out of the gas outlet of the movable gas introduction stem into a container held in the vaporization assembly housing is controlled by the movement of the movable gas introduction stem in response to the force applied by the user.

27. The carb cap according to claim 1, wherein the flexible diaphragm and the vaporization assembly attachment are one piece.

28. The carb cap according to claim 1, wherein the flexible diaphragm and the movable gas introduction stem are one piece.

29. A method of introducing gas flow into a vaporization assembly, the method comprising:
attaching the carb cap of claim 1 to the vaporization assembly of a vaporization device, and during operation of the vaporization device, moving the movable gas introduction stem to direct a flow of gas entering a container held in the vaporization assembly.

* * * * *